US011325367B2

(12) United States Patent
Krizan et al.

(10) Patent No.: US 11,325,367 B2
(45) Date of Patent: May 10, 2022

(54) SMOOTH FILM LAMINATED ELASTOMER ARTICLES

(71) Applicant: West Pharmaceutical Services, Inc., Exton, PA (US)

(72) Inventors: Jason Krizan, Elkton, MD (US); Douglas R. Duriez, Morgantown, PA (US); Liang Fang, Chesterbrook, PA (US); Kerry Drake, Red Hill, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 16/771,136

(22) PCT Filed: Dec. 17, 2018

(86) PCT No.: PCT/US2018/066078
§ 371 (c)(1),
(2) Date: Jun. 9, 2020

(87) PCT Pub. No.: WO2019/118983
PCT Pub. Date: Jun. 20, 2019

(65) Prior Publication Data
US 2021/0162725 A1    Jun. 3, 2021

Related U.S. Application Data

(60) Provisional application No. 62/599,259, filed on Dec. 15, 2017.

(51) Int. Cl.
*B32B 38/10* (2006.01)
*B29C 43/02* (2006.01)
(Continued)

(52) U.S. Cl.
CPC ......... *B32B 38/10* (2013.01); *A61M 5/31513* (2013.01); *B29C 43/003* (2013.01);
(Continued)

(58) Field of Classification Search
CPC ... B29C 43/003; B29C 43/203; B29C 43/206; B29C 2043/025; B29C 65/70;
(Continued)

(56) References Cited

U.S. PATENT DOCUMENTS 4,554,125 A    11/1985 Knapp
4,801,479 A    1/1989 Fielder et al.
(Continued)

FOREIGN PATENT DOCUMENTS

CN    101175527 A    5/2008
CN    101256313 A    9/2008
(Continued)

OTHER PUBLICATIONS

West Pharmaceutical Services Introduces West FluroTec Barrier Film; State-of-the-Art Parenteral Packaging Technology May Reduce Risk of Costly Drug Contamination, Oct. 27, 2003.
(Continued)

*Primary Examiner* — Atul P. Khare
(74) *Attorney, Agent, or Firm* — BakerHostetler

(57) ABSTRACT

A method for manufacturing at least one elastomeric article is provided. The method includes placing into a mold an assembly of an uncured elastomeric sheet, a first film fully covering the elastomeric sheet and a second film covering the first film, such that the second film is in contact with and positioned between the first film and an interior surface of the mold. The method further includes curing the assembly in the mold, such that the first film is laminated onto the elastomeric sheet thereby forming the at least one elastomeric article.

18 Claims, 22 Drawing Sheets

(51) Int. Cl.
  *B32B 27/08* (2006.01)
  *A61M 5/315* (2006.01)
  *B29C 43/00* (2006.01)
  *B32B 27/26* (2006.01)
  *B32B 27/30* (2006.01)
  *B32B 37/26* (2006.01)
  *B29C 65/70* (2006.01)
  *B29C 43/20* (2006.01)
  *B32B 37/00* (2006.01)
  *B29C 65/00* (2006.01)
  *B29K 27/18* (2006.01)
  *B29L 31/00* (2006.01)

(52) U.S. Cl.
  CPC .......... *B29C 43/02* (2013.01); *B29C 43/203* (2013.01); *B29C 65/70* (2013.01); *B29C 66/81265* (2013.01); *B32B 27/08* (2013.01); *B32B 27/26* (2013.01); *B32B 27/304* (2013.01); *B32B 37/0053* (2013.01); *B32B 37/26* (2013.01); *A61M 2207/10* (2013.01); *B29C 2043/025* (2013.01); *B29K 2027/18* (2013.01); *B29L 2031/7544* (2013.01); *B32B 2037/268* (2013.01); *B32B 2274/00* (2013.01); *B32B 2305/72* (2013.01); *B32B 2307/538* (2013.01); *B32B 2307/714* (2013.01); *B32B 2307/72* (2013.01); *B32B 2435/02* (2013.01); *B32B 2439/80* (2013.01); *B32B 2581/00* (2013.01)

(58) Field of Classification Search
  CPC ..... B29C 59/005; B29C 59/02; B29C 59/026; B29C 2059/023; B29C 66/81265; B32B 37/0053; B32B 2037/268; B32B 2305/72
  See application file for complete search history.

(56) References Cited

U.S. PATENT DOCUMENTS

| | | | |
|---|---|---|---|
| 4,824,631 A | 4/1989 | Yeager | |
| 4,956,141 A | 9/1990 | Allen et al. | |
| 4,997,423 A | 3/1991 | Okuda et al. | |
| 5,077,118 A * | 12/1991 | Hasegawa | B44C 1/10 428/149 |
| 5,078,941 A | 1/1992 | Tatsumi et al. | |
| 5,108,532 A | 4/1992 | Thein et al. | |
| 5,320,700 A | 6/1994 | Hall et al. | |
| 5,891,384 A | 4/1999 | Miyajima | |
| 6,645,635 B2 | 11/2003 | Muraki | |
| 6,866,919 B2 * | 3/2005 | Ikeguchi | B32B 27/08 174/258 |
| 8,499,957 B2 | 8/2013 | Kawachi | |
| 8,722,178 B2 | 5/2014 | Ashmead et al. | |
| 9,039,664 B2 | 5/2015 | Ogawa et al. | |
| 9,242,408 B2 | 1/2016 | Ussing | |
| 9,452,264 B2 | 9/2016 | Maeda et al. | |
| 10,265,894 B2 * | 4/2019 | Kawai | B32B 7/06 |
| 2008/0305300 A1 * | 12/2008 | Suto | B32B 27/12 428/141 |
| 2010/0264139 A1 | 10/2010 | Kawachi | |
| 2014/0062036 A1 | 3/2014 | Maeda et al. | |
| 2015/0165125 A1 | 6/2015 | Foucher et al. | |
| 2016/0022918 A1 | 1/2016 | Gunzel | |
| 2016/0287800 A1 | 10/2016 | Nakano et al. | |

FOREIGN PATENT DOCUMENTS

| | | |
|---|---|---|
| CN | 202996917 U | 6/2013 |
| CN | 103656803 A | 3/2014 |
| CN | 104160492 A | 11/2014 |
| CN | 104170101 A | 11/2014 |
| CN | 107385293 A | 11/2017 |
| EP | 0837770 A1 | 4/1998 |
| EP | 1060031 B2 | 12/2000 |
| EP | 2095836 A1 | 9/2009 |
| EP | 2944463 A1 | 11/2015 |
| EP | 3006069 A1 | 4/2016 |
| EP | 3028730 A1 | 6/2016 |
| JP | 05-147052 A | 6/1993 |
| JP | 2001310313 A * | 11/2001 |
| JP | 2014-213490 A | 11/2014 |
| JP | 2016209081 A | 12/2016 |
| WO | 96/40503 A1 | 12/1996 |
| WO | 03006083 A2 | 1/2003 |
| WO | 2011059823 A1 | 5/2011 |
| WO | 2013115331 A1 | 8/2013 |
| WO | 2014169977 A1 | 10/2014 |
| WO | 2014194918 A1 | 12/2014 |

OTHER PUBLICATIONS

Rodriguez et al., "Role of hydrophobicity on interfacial fluid flow: Theory and some application", The European Physical Journal. E, 37:57, 14 pages (Jun. 2014).
Int'l Search Report dated Apr. 4, 2019 in Int'l Application No. PCT/US2018/066078.

* cited by examiner

← → High Ra

↕ Low Ra

↕ High Ra

← → Low Ra

SMOOTH FILM LAMINATED ELASTOMER ARTICLES

CROSS-REFERENCE TO RELATED APPLICATIONS

This application is a section 371 of International Application No. PCT/US18/66078, filed Dec. 17, 2018, which was published on Jun. 20, 2019 under International Publication No. WO 2019/118983 A1, which claims priority to U.S. Provisional Patent Application No. 62/599,259, titled "Smooth Film Laminated Elastomeric Articles," filed on Dec. 15, 2017, the entire contents of which are incorporated herein by reference.

BACKGROUND OF THE DISCLOSURE

The present invention is generally related to elastomeric articles, and more particularly, to elastomeric stoppers and pistons.

To protect sensitive drug products from extractable and leachable substances originating from a container for the drug product, which includes an elastomer seal or other closure, e.g., stopper or piston, it is known to include a film laminate on the elastomer seal or closure on the drug contact surface (i.e., in between the drug and the elastomer) to improve product performance, and is an important risk mitigation strategy to avoid or reduce unwanted extractables and leachables from the elastomer. For example, many conventional plastic or glass syringe assemblies have either a coated or uncoated elastomeric piston. For coated pistons, the distal surface, typically referred to as the drug contact surface, is usually coated with an inert film in order to reduce drug interactions with the elastomeric material of the piston. The entire surface of the piston, and more particular the peripheral tubular surface, however, is usually not coated. That is, the cylindrical sidewalls, including sealing ribs, of conventional elastomer pistons are left with bare elastomer, in order to provide adequate sealing. This is also typically the case for coated vial stoppers. That is, the drug contact surface is coated with an inert film, but the bottom of the flange and external sidewalls that contact the vial remain uncoated to provide better sealing effect. As used herein, the sealing surface refers to the circumferential sidewall of a piston or stopper with or without sealing ribs.

One consequence of having bare elastomer in contact with the glass barrel is that frictional forces prevent smooth and easy operation of the syringe. As a result, conventionally, the syringe barrel is treated with silicone oil or silicone is "baked-on" it to reduce the static frictional force, which is referred to as the break-loose force, and to reduce the dynamic frictional force, which is referred to as the glide or extrusion force.

However, silicone oil has been known to interact with some biological drugs. Silicone oil has also been known to separate from the barrel and become injected into a patient with the drug. Moreover, regulatory guidance typically teaches away from using silicone oil in ophthalmic applications, because lasers are often used for surgery in and around the eye and silicone oil has been known to outgas under high temperatures which occur during laser surgery.

What is desired, therefore, is an elastomer which does not interact with the drug or which produces the fewest extractables and leachables. What is also desired is a container system that is not a source of silicone oil.

Another drawback associated with manufacturing both partial film laminated stoppers and pistons is that additional manufacturing steps are required, as compared to manufacturing processes for producing unlaminated or fully laminated stoppers and pistons. That is, the elastomeric article undergoes a so-called "two-step" process, in which the piston tip (distal end) or stopper bottom, the ends in contact with the drug product, are first partially cured with the film separately from the respective piston base or stopper flange, and then the piston tip and piston base or stopper bottom and stopper flange are combined and then fully cured in a subsequent step.

However, conventional stoppers and pistons typically do not include a film laminated over their entire external surface. This is because even minute imperfections in the laminated film layer would enable percolation of gasses or fluids past the seal between the laminated film layer and the container (i.e., a syringe, cartridge or vial) which may compromise the container closure integrity (CCI). In particular, scratches or small defects which result in a continuous path across the sealing surface, i.e., the interface between the film-side of an elastomer laminated with an inert film and the container (syringe, cartridge or vial) which prevents the drug from escaping to the outside of the container, can severely compromise CCI. For example, on a piston used in a syringe, an axial scratch, perpendicular to the sealing rib and parallel to the longitudinal axis of the syringe would create a path compromising CCI (see FIG. 4A). Scratches around the circumference of the piston, parallel to the sealing rib, may also compromise CCI (although such scratches may not necessarily cause CCI failure, such as drug leakage) (FIG. 4B). Also, a sufficiently high overall surface roughness (Ra) typically will still allow percolation of drug product or gas through a random path of roughness, and therefore compromise CCI.

In systems which use silicone, the silicone itself has been shown to reduce CCI issues. However, in silicone-free drug-containment systems, no silicone is present to reduce CCI issues.

Therefore, it would be desirable to provide a silicone-free drug-containment system, in which the closure (i.e., piston or stopper) is entirely film laminated, and in which the CCI at the interface of the sealing surface of the closure and container substrate is maintained at a sufficiently high level. Another benefit of having the entire or a large portion of piston or stopper coated with an inert film, is to protect the elastomer from unintended exposure to chemicals including solvents used in the manufacturing process, such as dimethyl sulfoxide (DMSO). DMSO has been known to cause rubber to swell, which may cause some dimensions of a stopper or piston to increase beyond suitable tolerances.

Therefore, what is also desired is a piston or stopper having adequate sealing properties which is entirely film-laminated, so that it may be made using a single curing process or step. In addition, it would be desirable to provide film laminated pistons or stoppers configured to be used in a silicone-free glass syringe and having similar sealing and frictional properties as a conventional piston made with the two-step process and coated with silicone oil, or using a syringe or cartridge barrel coated with silicone oil or having based on silicone.

BRIEF SUMMARY OF THE DISCLOSURE

One embodiment of the present invention is related to a method for manufacturing at least one elastomeric article comprising the steps of: placing into a mold an assembly of an uncured elastomeric sheet, a first film fully covering the elastomeric sheet and a second film covering the first film, such that the second film is in contact with and positioned between the first film and an interior surface of the mold; and curing the assembly in the mold, such that the first film is laminated onto the elastomeric sheet thereby forming the at least one elastomeric article.

Another embodiment of the present invention is directed to an elastomeric article for sealing a container comprising an elastomeric body having an external sidewall surface and an external crown surface, and a first fluoropolymer film layer having an internal surface and an external surface. The internal surface of the first fluoropolymer film layer is laminated to an entirety of the external sidewall and crown surfaces of the elastomeric body. The external crown surface of the first fluoropolymer film layer includes a drug contact surface configured to contact a drug contained in the container, and the external sidewall surface includes a sealing surface configured to contact an interior surface of the container.

Another embodiment of the present invention relates to a device for injecting a drug. The device comprises a silicone-free barrel and an elastomeric piston having a laminated film layer in contact with the silicone-free barrel. An interface between the laminated film layer and the silicone-free barrel having a seal which withstands leakage of gas of less than about $6 \times 10^{-6}$ atm*cc/sec.

Another embodiment of the present invention relates to a method for manufacturing an elastomeric article comprising the steps of: placing an uncured elastomeric sheet and a first film fully the elastomeric sheet into a mold; curing the elastomeric sheet with the first film in the mold into at least one elastomeric article; removing the elastomeric articles from the mold; and removing the first film from the at least one elastomeric article.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Figure 1:
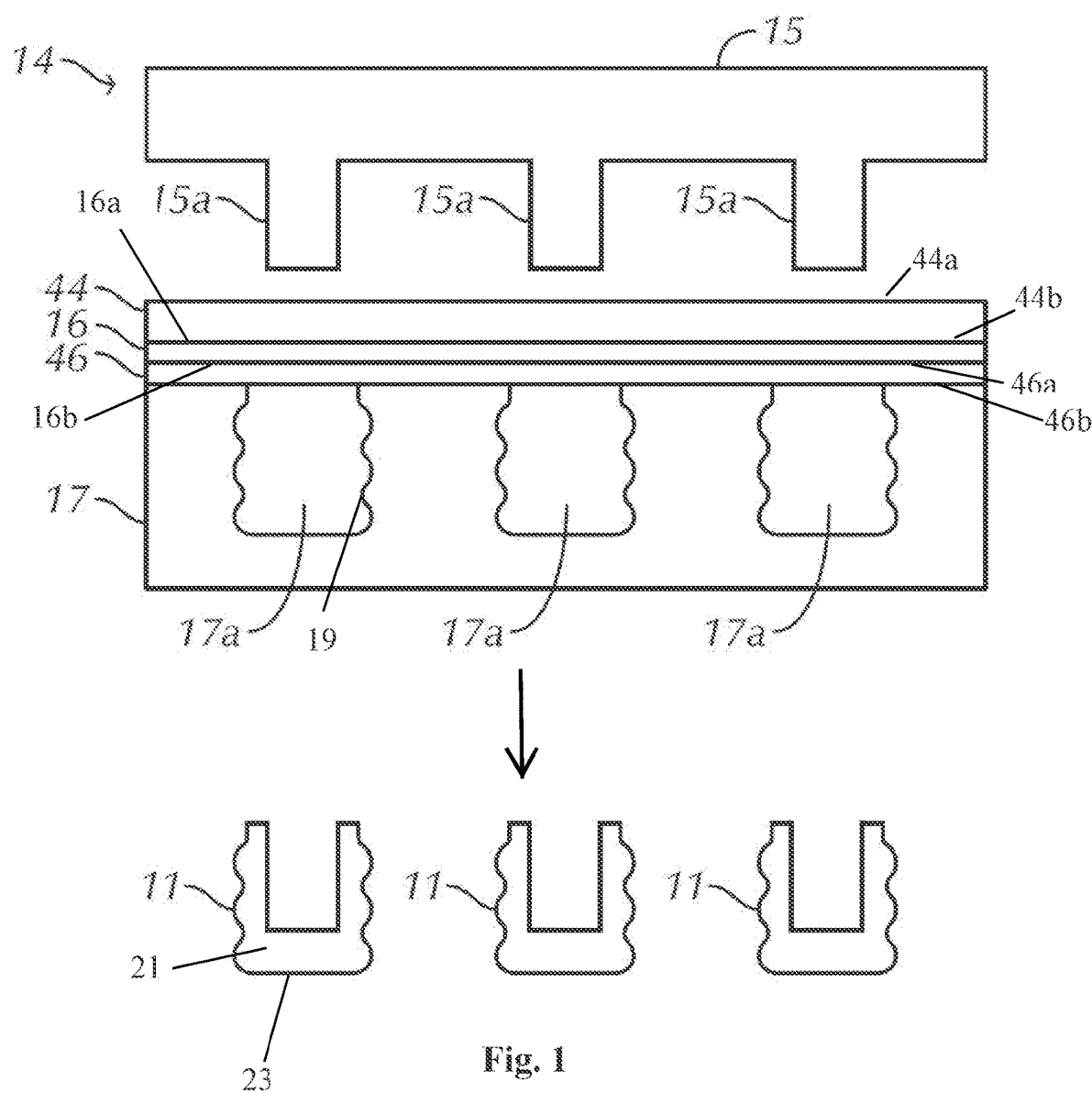
FIG. 1 depicts a one-step method of manufacturing an elastomeric article in accordance with an embodiment of the present invention.

Referring to FIG. 1, there is shown a method of manufacturing an elastomeric article, such as a piston 11, using a first mold 14, an elastomer sheet 44, a first film 16 and more particularly an inert film layer or barrier layer 16, and a second film 46 and more particularly a release film layer 46 in a one-step molding process, and more particularly in a one-step compression molding process. The first mold 14 includes an upper mold half 15 having a protrusion 15a and a lower mold half 17 having an open cavity 17a. The open cavity 17a is preferably an open heated mold cavity. In a preferred embodiment, the first mold 14 includes a plurality of upper and lower mold halves 15, 17 arranged in an array.

The elastomer sheet 44 is preferably formed of one or more elastomeric materials in a partially cured stage. In a preferred embodiment, the elastomeric material is either a thermoset elastomer or a thermoplastic elastomer (TPE). The elastomeric material used for the elastomeric closure can be, for example, a synthetic or natural rubber, such as butyl rubber, isoprene rubber, butadiene rubber, halogenated butyl rubber (e.g., bromobutyl rubber), ethylene propylene terpolymer, silicone rubber, combinations thereof and the like. Preferably, the elastomeric material is a butyl or halobutyl elastomer.

The inert film layer 16 is preferably formed of a polymer, and more particularly a highly inert polymer with good barrier properties and lubricity. The film 16 preferably is an olefin polymer and could include a cyclic olefin polymer. More preferably, the inert film layer 16 is formed of a fluoropolymer, such as tetrafluoroethylene or ethylene tetrafluoroethylene. Some non-limiting examples of polymers that may be used to form the inert film layer 16 include tetrafluoroethylene, polytetrafluoroethylene (PTFE), ethylene tetrafluoroethylene (ETFE), fluorinated ethylene propylene (FEP), polyvinylidene fluoride (PVF), polyvinylidene difluoride (PVDF), polychlorotrifluoroethylene (PCTFE), perfluoroalkoxy alkanes (PFA), ethylene chlorotrifluoroethylene (ECTFE), perfluoroelastomer (FFPM), fluoroelastomer polymer (FPM), polyethylene (PE), cyclic olefin polymer (COP), cyclic olefin copolymer (COC) and polypropylene (PP). The inert film layer 16 preferably has a thickness of from 0.5 μm to 300 μm, more preferably from 10 μm to 150 μm, and most preferably from 25 μm to 100 μm.

An even wider array of polymers are suitable for use in forming the release film layer 46, because the chemical requirements are different. That is, all of the above exemplary polymers identified for the material of the inert film layer 16 may also be used to form the release film layer 46. In addition, high temperature-compatible polymers, such as polyimides or silicones, are also suitable for use in forming the release film layer 46. Similar to the inert film layer 16, the release film layer 46 preferably has a thickness of from 0.5 μm 1 to 300 μm, more preferably from 10 μm to 150 μm, and most preferably from 25 μm to 100 μm.

The elastomer sheet 44 has a first surface 44a and an opposing second surface 44b. The inert film layer 16 has a first surface 16a and an opposing second surface 16b. The release film layer 46 has a first surface 46a and an opposing second surface 46b. The first surface 16a of the inert film layer 16 may be surface modified/treated to have a lower water contact angle and higher surface energy than unmodified second surface 16b. Preferably, the first surface 16a of the inert film layer 16 is etched, and more preferably plasma etched. Surface modification/treatment of the first surface 16a of the inert film layer 16 may permit it to bond to the elastomer sheet 44 strongly after compression molding. Because the second surface 16b of the inert film layer 16 is unmodified, it has a higher water contact angle and lower surface energy, which allows it to be more easily detached from an untreated side of another film, such as release film layer 46

The elastomer sheet 44, inert film layer 16, and release film layer 46 may be firmly joined with each other or independent from one another, in this order, and placed loosely on top of each other when introduced into the first mold 14. More particularly, for placement in the mold 14, the release film layer 46 is arranged such that the second surface 46b will contact the interior surface 19 of an open cavity 17a of the lower mold half 17; the inert film layer 16 is arranged such that the second surface 16b of the inert film layer 16 is in contact with the first surface 46a of the release film layer 46, and more preferably entirely covered by the first surface 46a of the release film layer 46; and the elastomer sheet 44 is arranged such that the first surface 44a is arranged so as to contact a protrusion 15a of the upper mold half 15 and the second surface 44b of the elastomer sheet 44 is in contact with the first surface 16a of the inert film layer 16, and more preferably the entirety of the second surface 44b of the elastomer sheet 44 is covered by the first surface 16a of the inert film layer 16. The two mold halves 15, 17 are then brought into contact with each other, such that each protrusion 15a contacts the first surface 44a of the elastomer sheet 44 and forces the layered arrangement of the elastomer sheet 44, inert film layer 16 and release film layer 46 into the open cavity 17a, so as to compress and mold the arrangement of the elastomer sheet 44, inert film layer 16, and release film layer 46 within each open cavity 17a in a single compression molding step.

This compression molding step is carried out at a temperature of 120° C. to 310° C. and a pressure of about 40 to 350 kg/cm² for a duration of a few seconds to 30 minutes. More preferably, the single compression molding step is carried out at a temperature of about 120° C. to 220° C. and a pressure of about 40 to 70 kg/cm² for a duration of about 30 seconds to 30 minutes. Most preferably, the single compression molding step is carried out at a temperature of about 140° C. to 220° C. and a pressure of about 40 to 70 kg/cm² for duration of about 2 to 15 minutes.

In a preferred embodiment, the compression molding step is carried out at a temperature of 160° C. to 165° C. and a pressure of 50 kg/cm² for a duration of about 15 minutes.

In another preferred embodiment, the compression molding step is carried out at a temperature of 160° C. to 175° C. and a pressure of about 40 to 70 kg/cm² for a duration of about 8 minutes.

During the compression molding step, the elastomeric sheet 44 is vulcanized under the influence of heat and pressure and is non-detachably joined with the inert film layer 16. More particularly, the elastomeric sheet 44 forms the body 21 of the piston 11 and the inert film layer 16 becomes a laminated film 23 non-detachably formed over the surface, and more preferably the sidewall and crown surfaces of the body 21. This process occurs below the melting temperature of both the inert film layer 16 and the release film layer 46 so that the films do not fuse together. Thus, the release film layer 46, on the other hand, becomes detachably joined to the laminated film layer 23. If a film is not melted, the layers can be separated. Different films can be used for the release layer than the film layer on the elastomeric article (dissimilar chemistry and/or higher melting points). For example, polyamide film is used as a release layer in many composites, which melts above 340° C.

After curing or vulcanization, the piston 11 is removed from the first mold 14 and the release film layer 46 is then peeled away from the piston 11. The release film layer 46 does not adhere to the inert film layer 16, as such, it can be mechanically separated from the inert film layer 16 as a continuous sheet or as cut portions from the individual pistons by, for example, grasping and pulling, blowing with fluid, or peeling by abrasion, among other techniques.

Prior to curing of the assembly of the elastomeric sheet 44, inert film layer 16 and release film layer 46 in the molding process, the inert film layer 16 has a surface roughness characterized by a first peak density. After the curing process and removal of the release film layer 46, the inert film layer 16, and more particularly the laminated film layer 23, has a surface roughness characterized by a second peak density, and the second peak density is increased relative to the first peak density. Preferably, the peak density of the inert film layer 16 is increased by at least 3%, and more preferably by at least 25%, after the curing process and removal of the release film layer 46. More particularly, the peak density of the inert film layer 16 is preferably increased by 3% to 165%, and more preferably by 25% to 35%, after the curing process and removal of the release film layer 46.

Although the process is discussed in terms of producing a piston 11, a skilled artisan would readily appreciate that the same process could be used for producing other elastomeric articles, such as a stopper or other closures.

Figure 2:
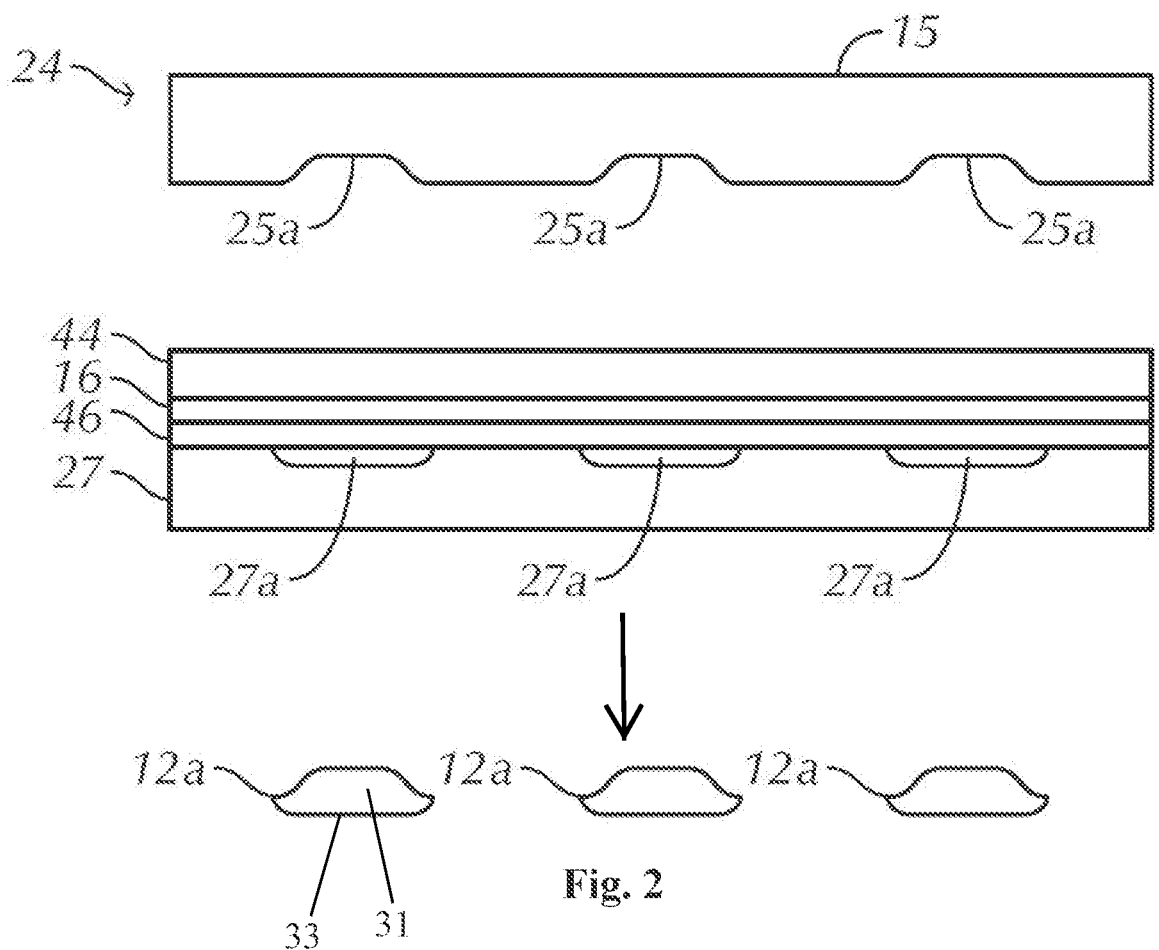
FIG. 2 depicts the first step of a two-step method of manufacturing an elastomeric article in accordance with an embodiment of the present invention.
Figure 3:
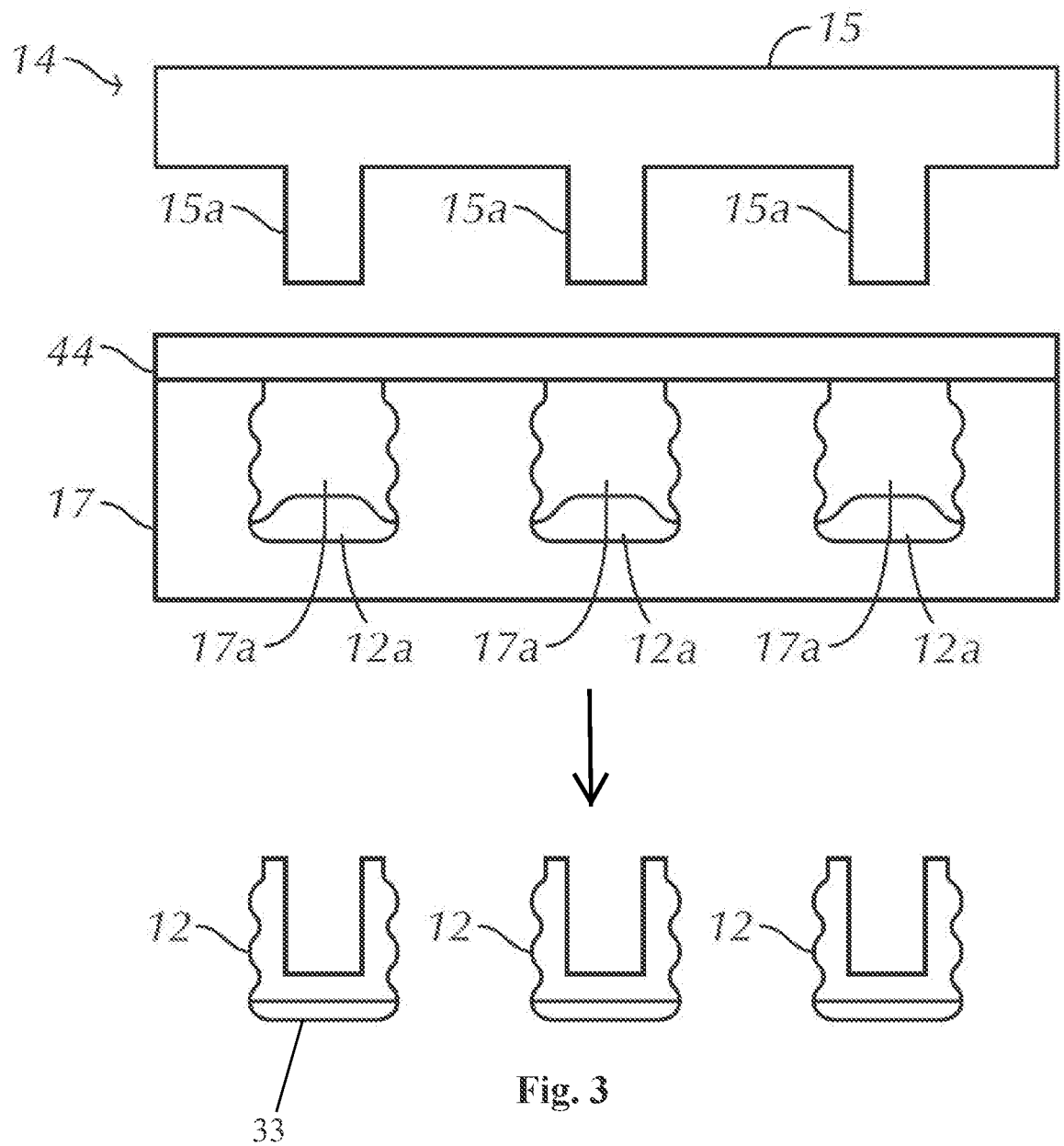
FIG. 3 depicts the second step of the two-step method of manufacturing an elastomeric article in accordance with an embodiment of the present invention.
Figure 4A:
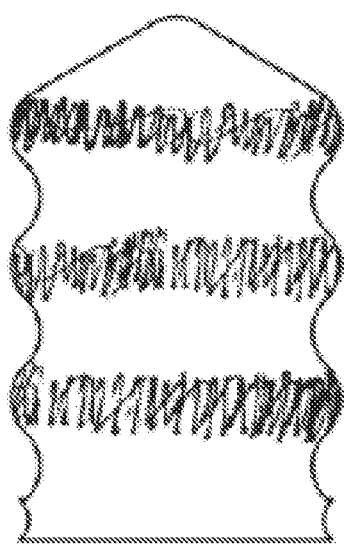
FIG. 4A shows a prior art piston having axial scratches perpendicular to the sealing rib and parallel to the axis of rotational symmetry which create a path compromising CCI.
Figure 4B:
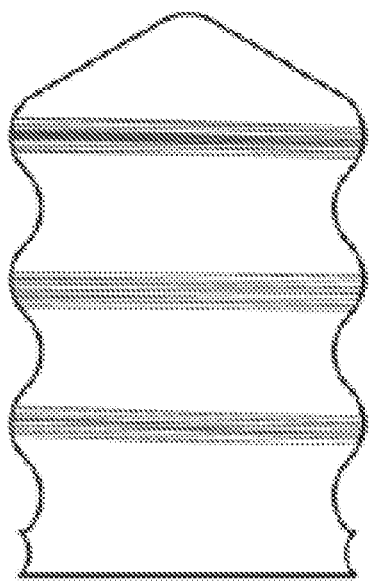
FIG. 4B shows a prior art piston having scratches around the circumference of the piston parallel to the sealing rib, which may compromise CCI.

Referring to FIGS. 2 and 3, there are shown methods of manufacturing an elastomeric article, such as a piston 12, according to another embodiment of the present invention. The process of FIG. 2 utilizes a second mold 24 that is sized and shaped to form a molded portion of an elastomeric article, as a piston crown 12a. The mold 24 thus serves as the initial mold for the manufacturing process. The process of FIG. 3 uses the mold 14 (i.e., the mold shown in FIG. 1) that is sized and shaped to form the whole elastomeric article (e.g., the piston 12). FIGS. 2 and 3 together illustrate a two-step molding process, and more particularly in a two-step compression molding process, according to an embodiment of the present invention.

Referring to FIG. 2, the mold 24 used for the first step of the two-step molding process includes an upper mold half 25 having an open cavity 25a and a lower mold half 27 having an open cavity 27a. The open cavities 25a, 27a are preferably open heated mold cavities. In a preferred embodiment, the first-step mold 24 includes a plurality of upper and lower mold halves 25, 27 arranged in an array. As with the one-step molding process, the elastomer sheet 44, the inert film layer 16, and the release film layer 46 may be firmly joined with each other or independent from one another, in this order, and placed loosely on top of each other when introduced into the second mold 24. The arrangement of the elastomer sheet 44, the inert film layer 16, and the release film layer 46 is the same as described above with respect to FIG. 1.

The process conditions for the molding step shown in FIG. 2 are the same as those discussed above for the one-step process of FIG. 1. As with the one-step process of FIG. 1, the elastomeric sheet 44 is vulcanized under the influence of heat and pressure and is non-detachably joined with the inert film layer 16, such that the vulcanized elastomeric material forms the body 31 of the piston crown 12a and the inert film layer 16 becomes a laminated film layer 33 non-detachably formed on the surface of the piston crown 12a (i.e., a laminated piston crown 12a). The release film layer 46, on the other hand, is detachably joined to the laminated film layer 33.

After vulcanization, the laminated piston crown 12a is removed from the mold 24 with the release film layer 46 intact on the laminated piston crown 12a. Next, the assembly of the laminated piston crown 12a and the release film layer 46 is trimmed and placed into the mold 14, as shown in FIG. 3, such that the release film layer 46 is in contact with the interior surface 19 of an open cavity 17a of the lower mold half 17 and the release film layer 46 is sandwiched between the laminated piston crown 12a and the open cavity 17a. In the two-step process of FIGS. 2 and 3, therefore, the mold 14 is a second-step mold.

Next, a second elastomeric sheet 44 is placed in the first mold 14, and more particularly over the open cavities 17a of the lower mold half 17. The two mold halves 15, 17 are then brought into contact with each other, such that each protrusion 15a contacts the first surface 44a of the second elastomer sheet 44 and forces the material of the second elastomer sheet 44 into the open cavity 17a and into contact with the laminated piston crown 12a, so as to compress and mold the arrangement of the second elastomer sheet 44 and the laminated piston crown 12a within each open cavity 17a in compression molding step. Vulcanization proceeds as described above with respect to FIG. 1, in order to produce a piston 12 having a removable release film layer 46 for masking the crown portion 12a in subsequent operations (such as an operation to produce a piston having silicone oil on only the exposed elastomer sides, but not on the laminated crown portion 12a).

Prior to curing of the assembly of the elastomeric sheet 44, inert film layer 16 and release film layer 46 in the molding process, the inert film layer 16 has a surface roughness characterized by a first peak density. After the curing process and removal of the release film layer 46, the inert film layer 16, and more particularly the laminated film layer 33, has a surface roughness characterized by a second peak density. The second peak density is increased relative to the first peak density. Preferably, the peak density of the inert film layer 16 is increased by at least 3%, and more preferably by at least 25%, after the curing process and removal of the release film layer 46. More particularly, the peak density of the inert film layer 16 is preferably increased by 3% to 165%, and more preferably by 25% to 35%, after the curing process and removal of the release film layer 46.

It will be understood that the first-step mold 24 may alternatively be sized and shaped to form a different portion of a different elastomeric article (e.g., the body of a stopper), instead of a piston crown 12a, and the second-step mold 14 may be sized and shaped to form a different elastomeric article instead of a piston.

Molding an elastomeric article, such as a piston or a stopper, in a two-step process produces an article having a drug interface portion coated with the inert film 16 and the remaining surface of the elastomeric article being uncovered (i.e., bare elastomer).

The resulting elastomeric article 11, 12 produced by the methods of the present invention is a smooth film-laminated elastomeric article. In one embodiment, the resulting elastomeric article 11, 12 is a silicone-free elastomeric article. The release film layer 46, which is sandwiched between the elastomeric sheet 44 covered with the inert film layer 16 and the mold cavity surface 19, protects the smooth film-laminated article (i.e., the piston 11) from damage during the manufacturing process, such as damage that might occur to the laminated film 23, 33 from sliding past the mold surface 19 during the molding and/or demolding steps. The release film layer 46 also protects the laminated film 23, 33 from any texture which would have been imparted to it by the mold surface 19 (i.e., it is a mechanical analogy to a low pass filter). The use of the release film layer 46 also protects the laminated film 23, 33 from any material contamination which might be imparted to it by the mold surface 19, such as processing aids used in the molding process, adhered elastomer, or any other environmental contamination. The use of the release film layer 46 creates a unique surface morphology as a result of the intimate surface-to-surface interfacial contact of the laminate films 23, 33 and the release film layer 46 and their subsequent separation.

Figure 13:
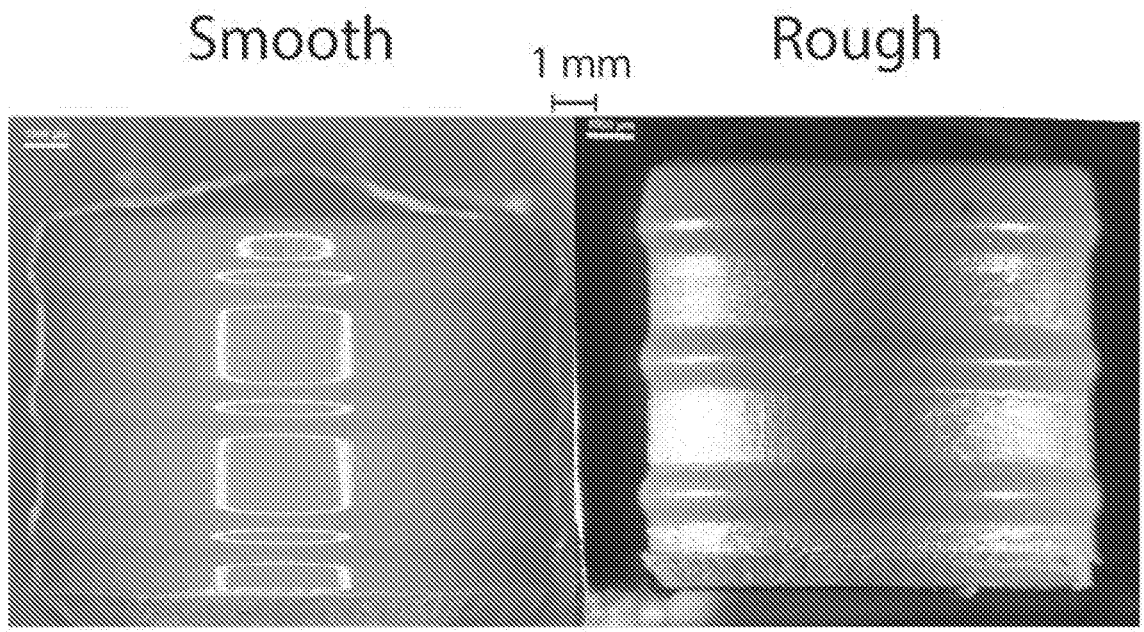
FIG. 13 shows optical microscopy images of an elastomeric piston according to the present invention, which has an improved surface finish, as compared to those prepared by a conventional process not involving a release film layer.

Also, use of the release film layer 46 gives the external surface of the laminated film layer 23, 33 a mirror-like finish. Thus, elastomeric articles made according to the invention have an exterior surface, and more particularly, an exterior sealing surface, comprised of a laminated film having a mirror-like finish or that substantially-free of striations or substantially smooth. FIG. 13 compares the texture of a plunger with a laminated film according to the invention to that of a conventional laminated plunger and shows that a plunger according to the invention has an exterior surface that is smooth or with a mirror-like surface (left hand side), as compared to a conventional film laminated plunger with an exterior surface that is rough, with striations and not mirror-like (right hand side).

Specific embodiments of the invention will now be described in terms of the following non-limiting examples and experiments.

Examples 1-4

Figure 5A:
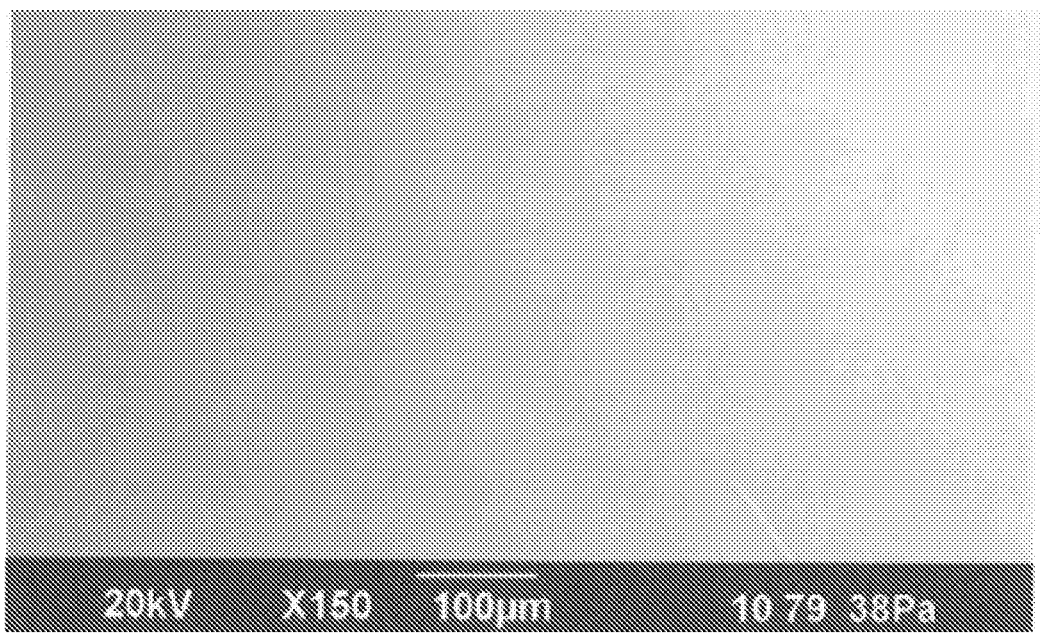
FIGS. 5A and 5C are scanning electron microscope (SEM) images (150× magnification) of the drug contact surface of an elastomeric piston produced by a method in accordance with an embodiment of the present invention.
Figure 5B:
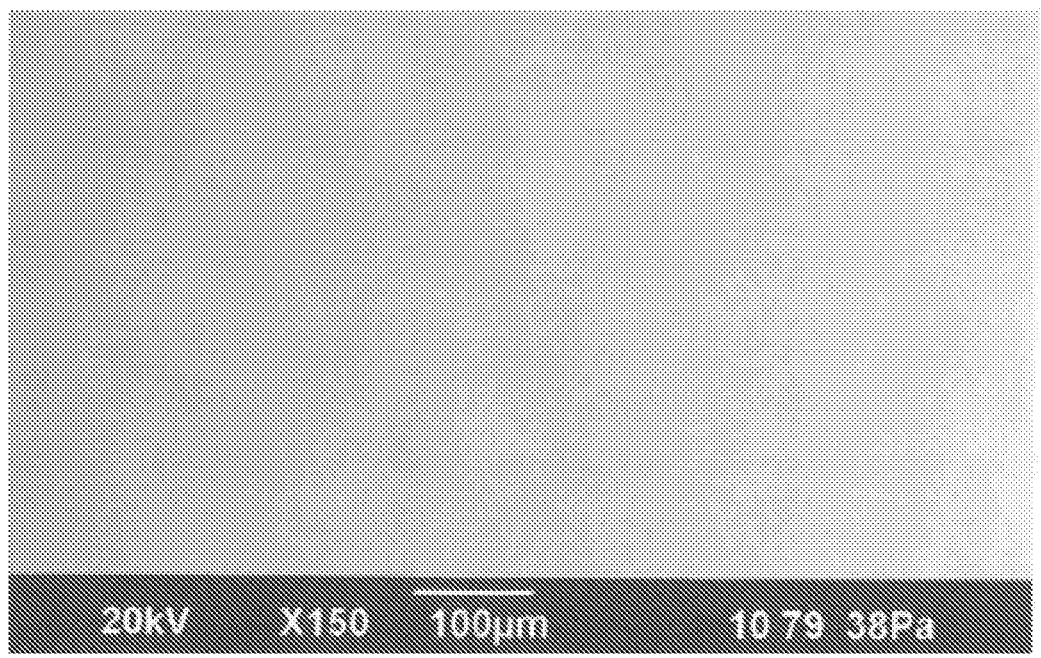
FIGS. 5B and 5D are SEM images (150× magnification) of the circumferential side surface, and more particularly a sealing rib, of an elastomeric piston produced by a method in accordance with an embodiment of the present invention.
Figure 5C:
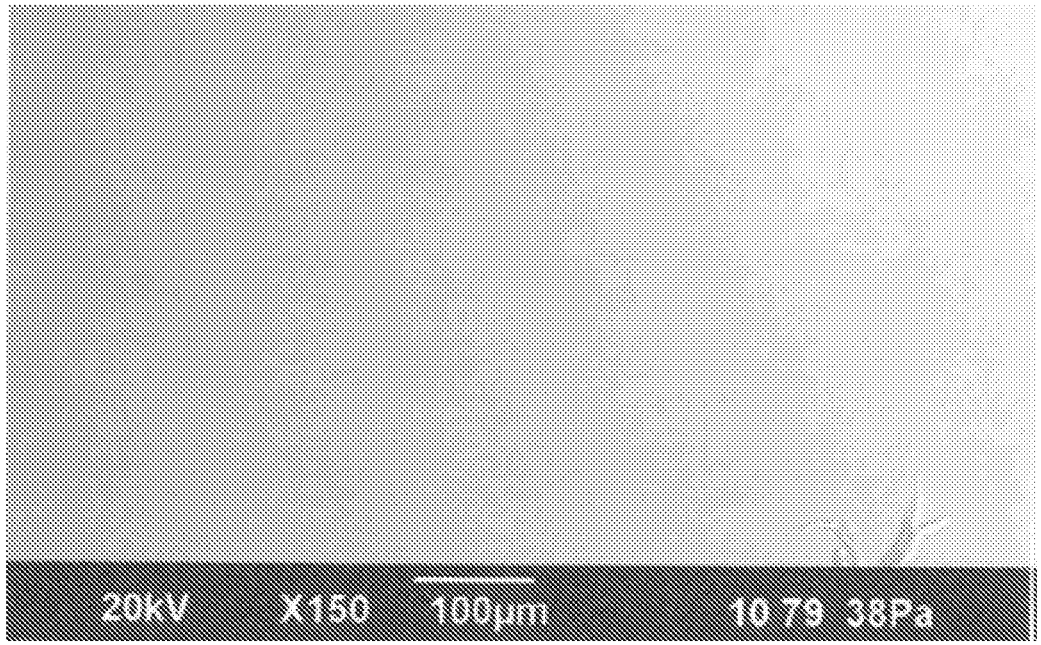
Figure 5D:
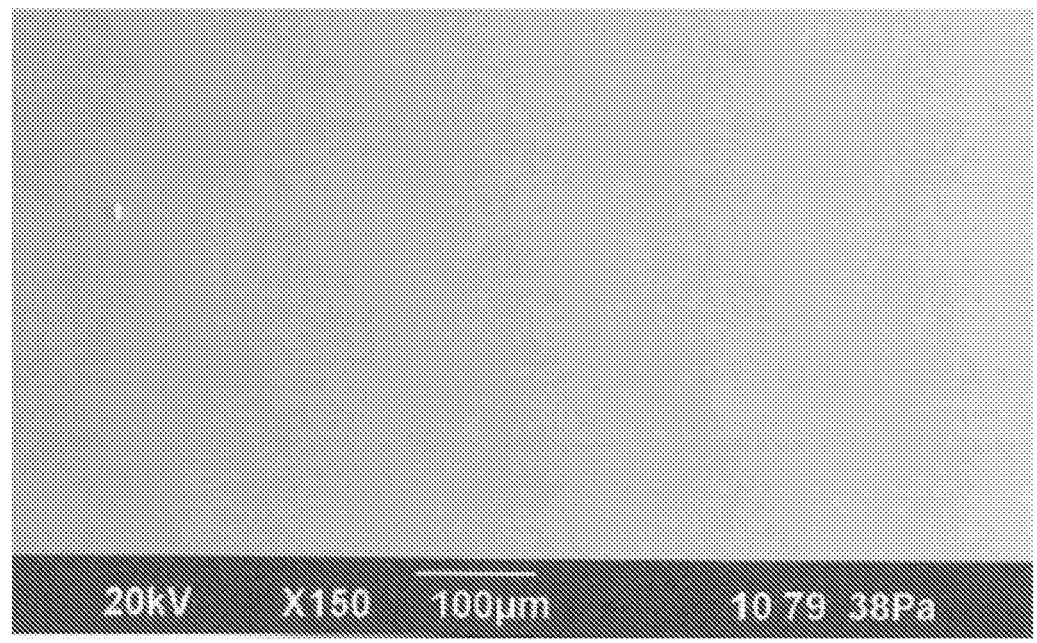
Figure 6A:
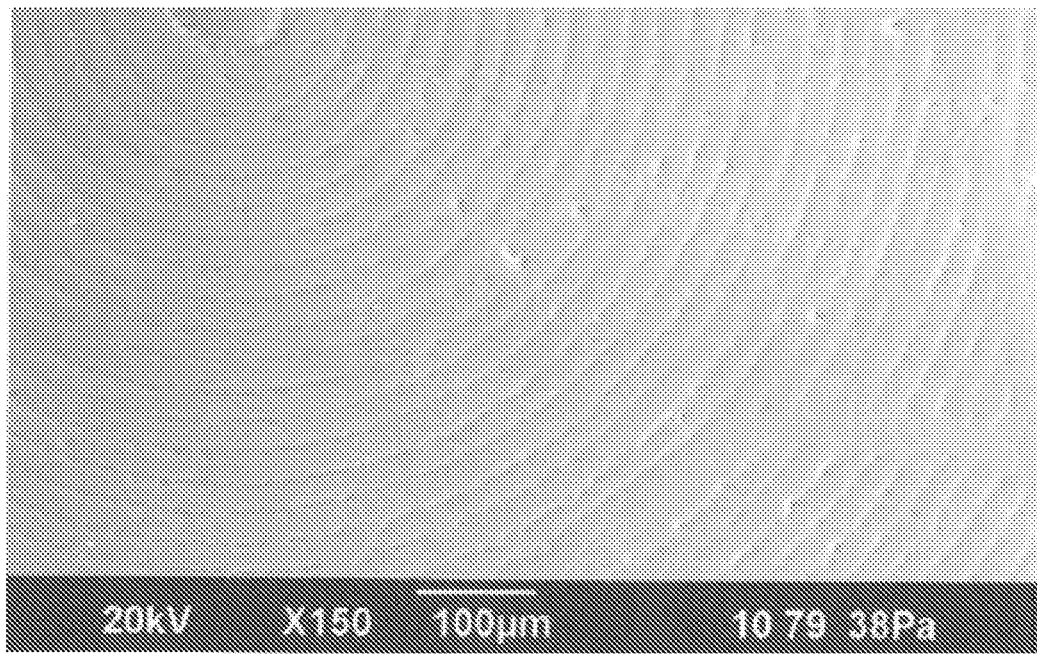
FIGS. 6A and 6C are SEM images (150× magnification) of the drug contact surface of an elastomeric piston produced by a method which did not utilize a release film layer.
Figure 6B:
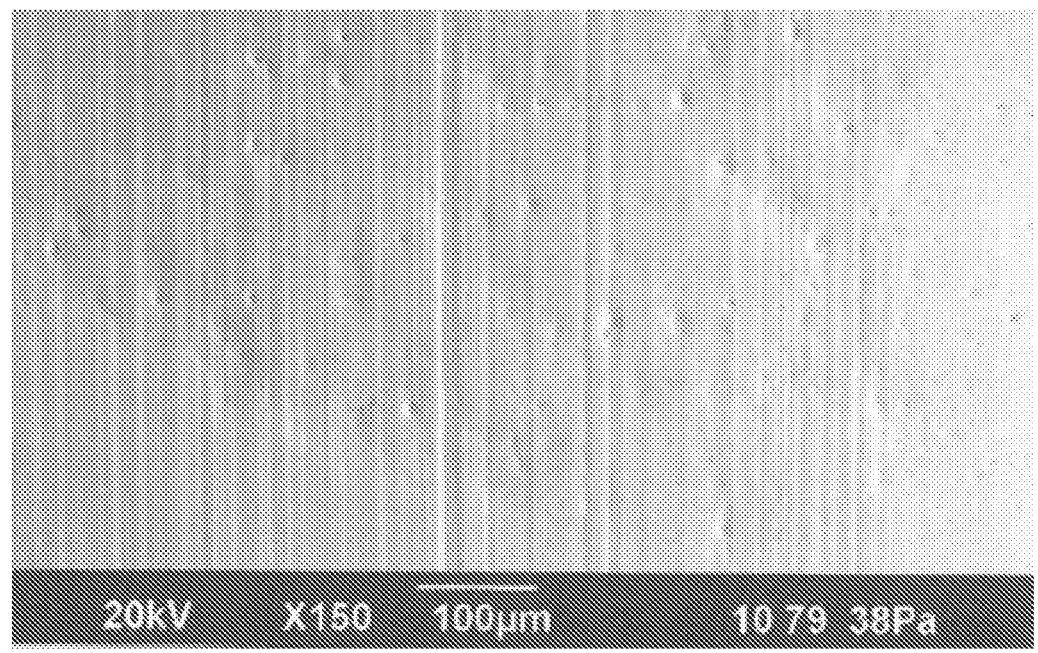
FIGS. 6B and 6D are SEM images (150× magnification) of the circumferential side surface, and more particularly a sealing rib, of an elastomeric piston produced by a method which did not utilize a release film layer.
Figure 6C:
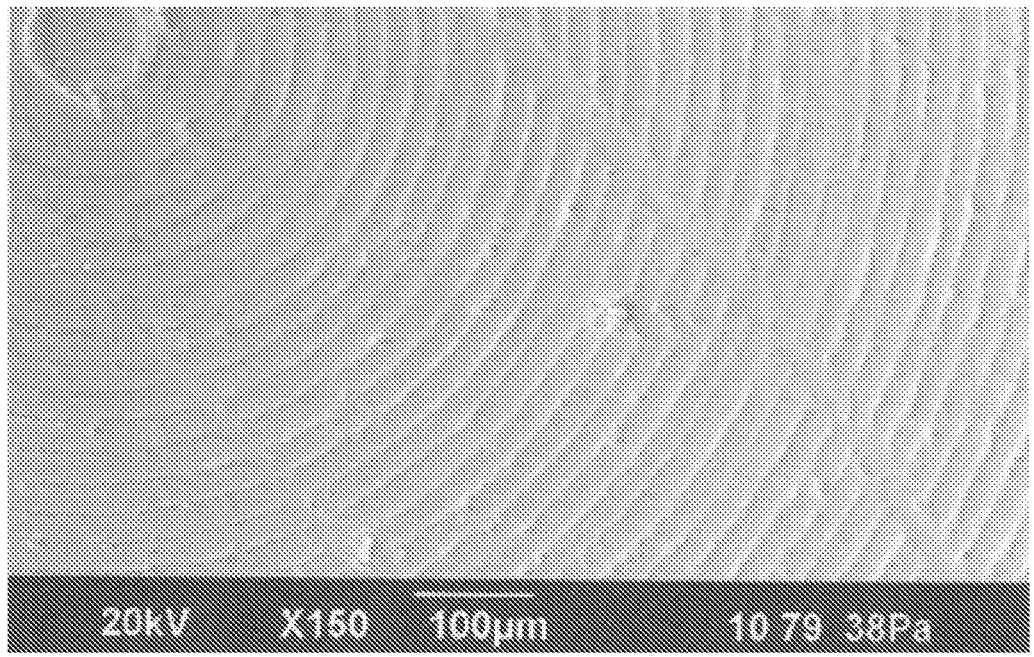
Figure 6D:
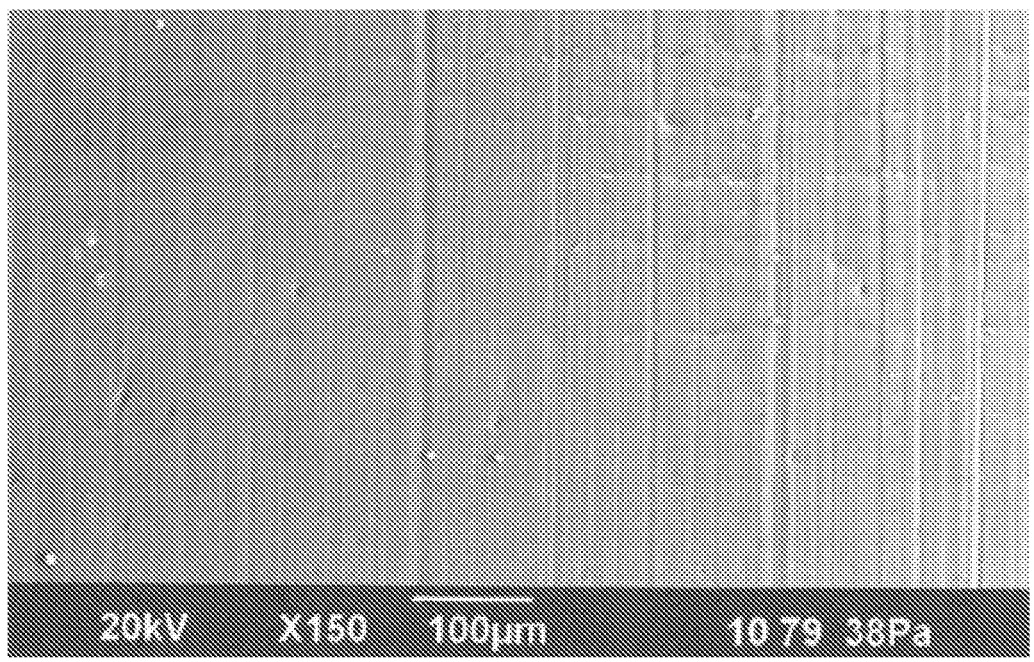

Examples 1-4 below utilize four elastomeric pistons laminated with PTFE (i.e., a laminated PTFE film layer covering the body of the piston and thus forming the external sidewall and crown surfaces of the piston) and produced according to the process described above with respect to FIG. 1 with a release film layer of ETFE. For comparison purposes, four elastomeric pistons each having a PTFE barrier layer were produced according to the same process, except that a release film layer was not utilized (hereinafter referred to as Comparative Examples 1-4). The piston crown (shown in FIGS. 5A and 5C) and the circumferential sealing surface, and more particularly the primary sealing rib (shown in FIGS. 5B and 5D) of Examples 1-4 have an extremely smooth laminated film surface with no clear texture, marks, or striations on the surfaces. In contrast, the laminated film surfaces of the piston crown (shown in FIGS. 6A and 6C) and the circumferential sealing surface, and more particularly the primary sealing rib (shown in FIGS. 6B and 6D) of each of the Comparative Examples 1-4 has significant surface features, in the form of broken circles, slashes and striations of random depth and length, pitting of random sizes and depth, flat areas, broken shallow trenches and the like.

Test 1

A 5-mL elastomeric piston having a laminated PTFE barrier layer was produced according to the process described above with respect to FIG. 1, utilizing a release film layer formed of ETFE having a 2 mil (~50 μm) thickness (the analysis was performed on different areas of the first rib (i.e., the rib closest to the drug contact surface) of the piston to show variation across the surface, and is accordingly referred to in Table 1 as Inventive Samples A and B) (Inv. Samples A and B). For comparison purposes, a bare elastomeric piston was produced using the same process parameters as that used to produce Inv. Samples A and B, but no laminated film layer or release film layer was utilized (referred to in Table 1 as Comparative Sample 1) (Comp. Sample 1); an elastomeric piston provided with a laminated PTFE barrier film was produced according to the same process parameters as used to produce Inv. Samples A and B, except that a release film layer was not utilized (referred to in Table 1 as Comparative Sample 2) (Comp. Sample 2); and a PTFE film before molding was provided (referred to in Table 1 as Comparative Sample 3) (Comp. Sample 3).

Figure 7:
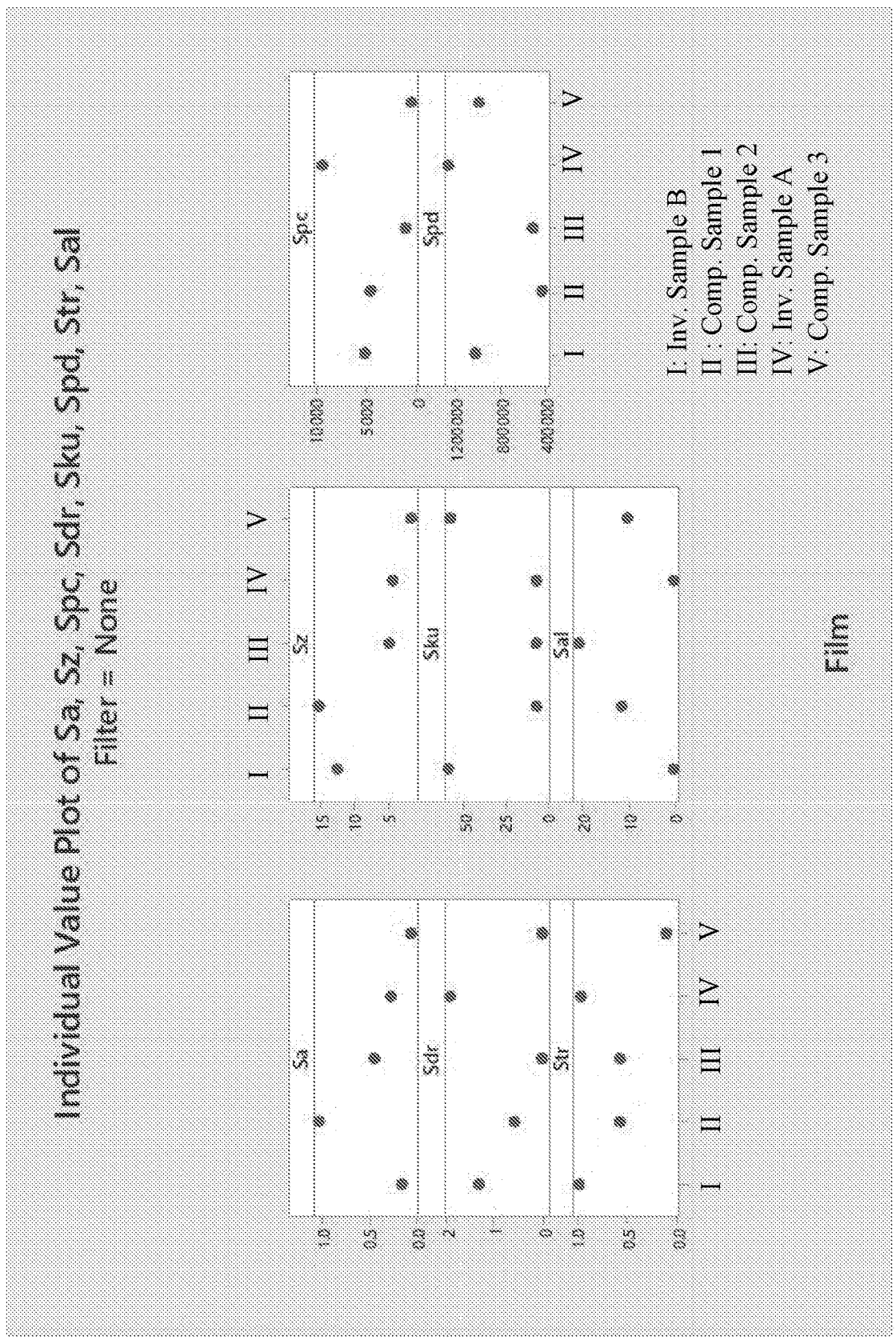
FIG. 7 is a graphical plot of various area roughness parameters of samples of elastomeric articles manufactured by a method in accordance with an embodiment of the present invention and comparative articles.
Figure 8:
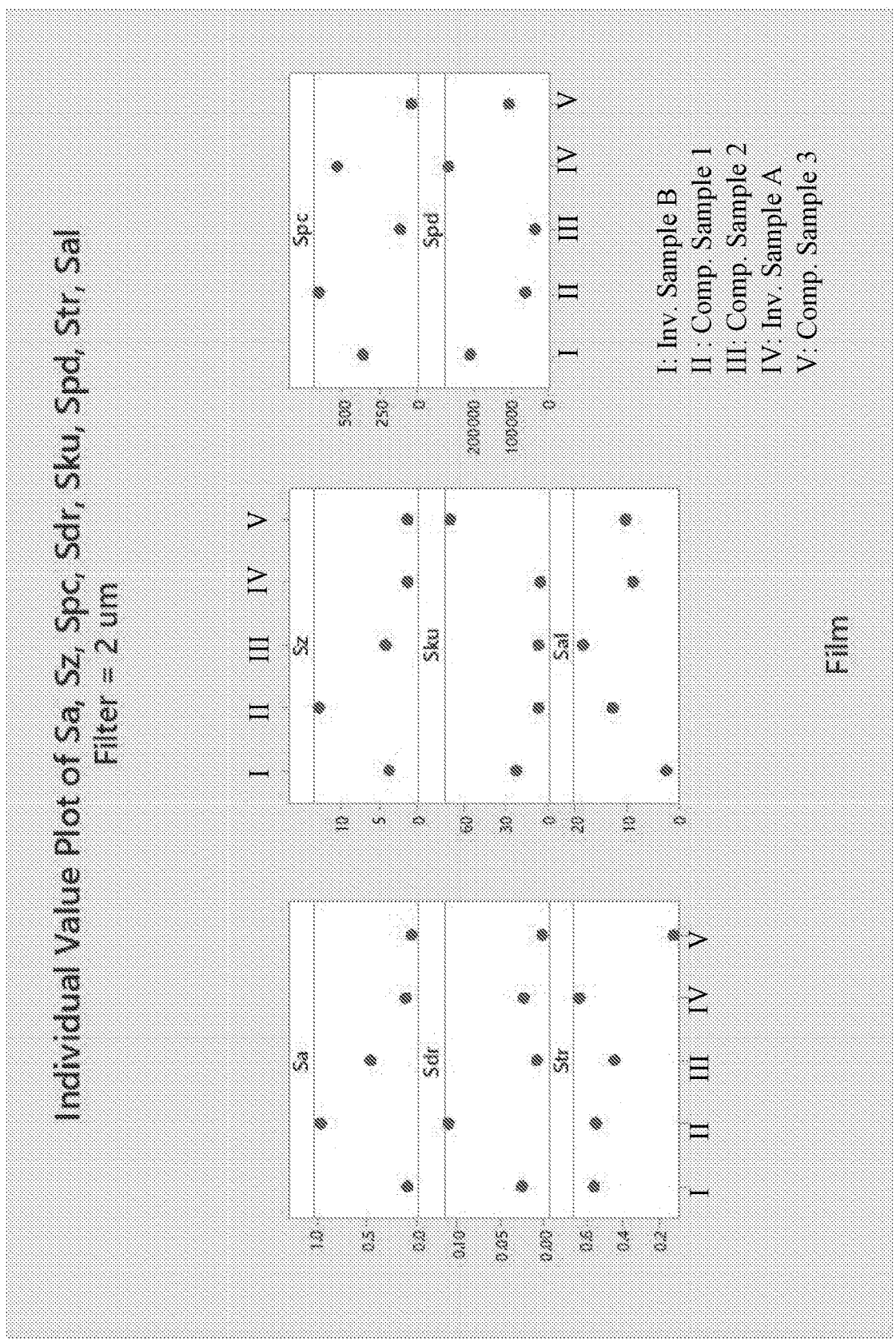
FIG. 8 is a graphical plot of various area roughness parameters of samples of elastomeric articles manufactured by a method in accordance with an embodiment of the present invention and comparative articles, with application of a 2 μm Gaussian filter.
Figure 9:
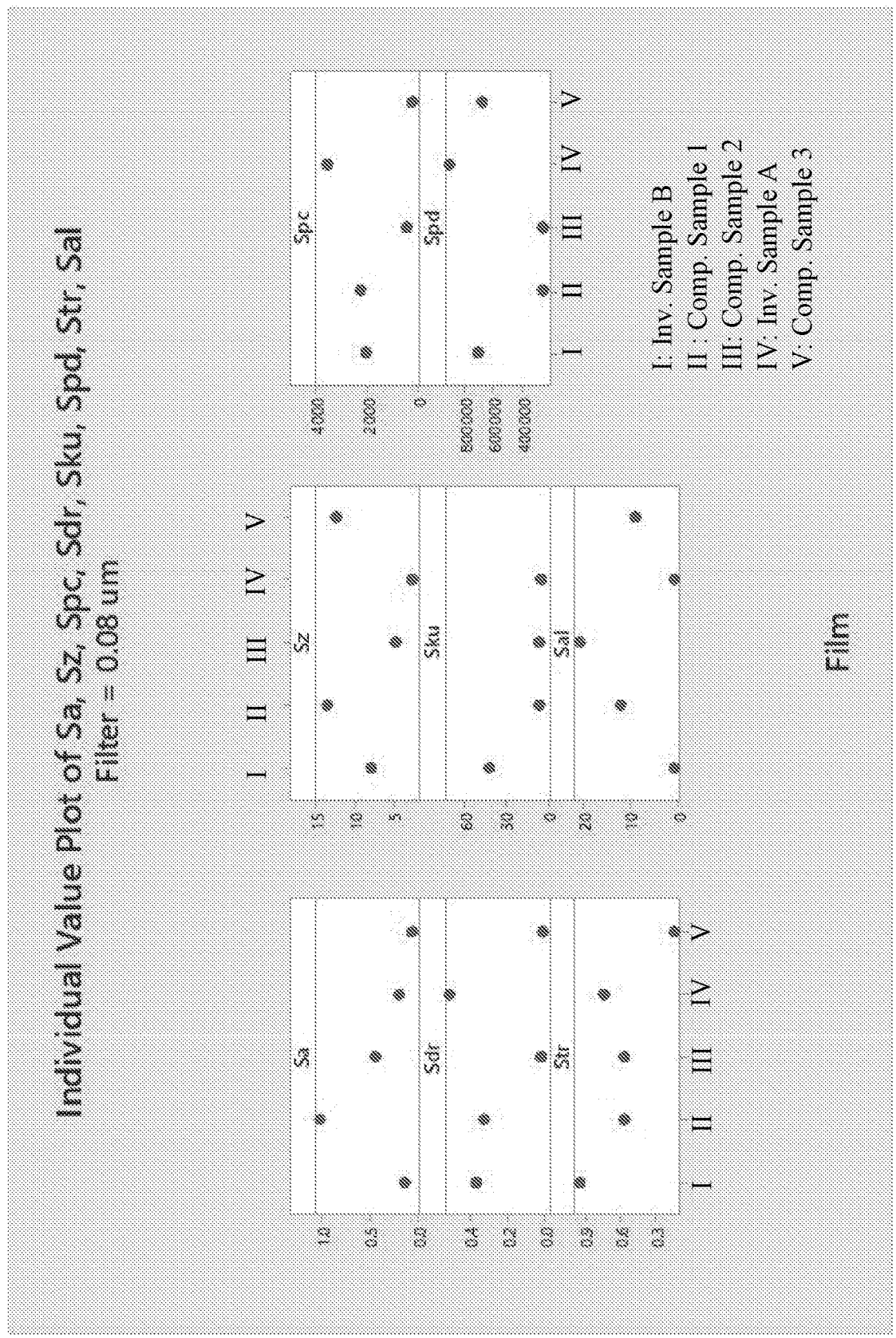
FIG. 9 is a graphical plot of various area roughness parameters of samples of elastomeric articles manufactured by a method in accordance with an embodiment of the present invention and comparative articles, with application of a 0.08 μm Gaussian filter.

The surface texture of each piston and film was measured using a Keyence 3D laser scanning confocal microscope. To determine the area roughness parameters, the measurement results were evaluated using ISO 25178 Surface Texture standard in three different manners: first, with no filter applied, as reflected by Ex. A-1 through A-5; second, with a 2 μm Gaussian filter applied to eliminate the high frequency component of the measurement and separate waviness from roughness, in accordance with JIS B 0632:2001 (ISO 11562:1996) and ISO 16610-21:2011, as reflected by Ex. B-1 through B-5; and third, with a 0.08 μm Gaussian filter applied to eliminate the high frequency component of the measurement and separate waviness from roughness, in accordance with JIS B 0632:2001 (ISO 11562:1996) and ISO 16610-21:2011, as reflected by Ex. C-1 through C-5, in order to determine area roughness parameters of each piston and film. The area roughness parameters are summarized in Table 1 and are graphically plotted in FIGS. 7-9, where the y-axis is parallel to the longitudinal axis of the piston, such that the drug contact surface of the piston is positioned proximate the top of each graph.

Figure 10:
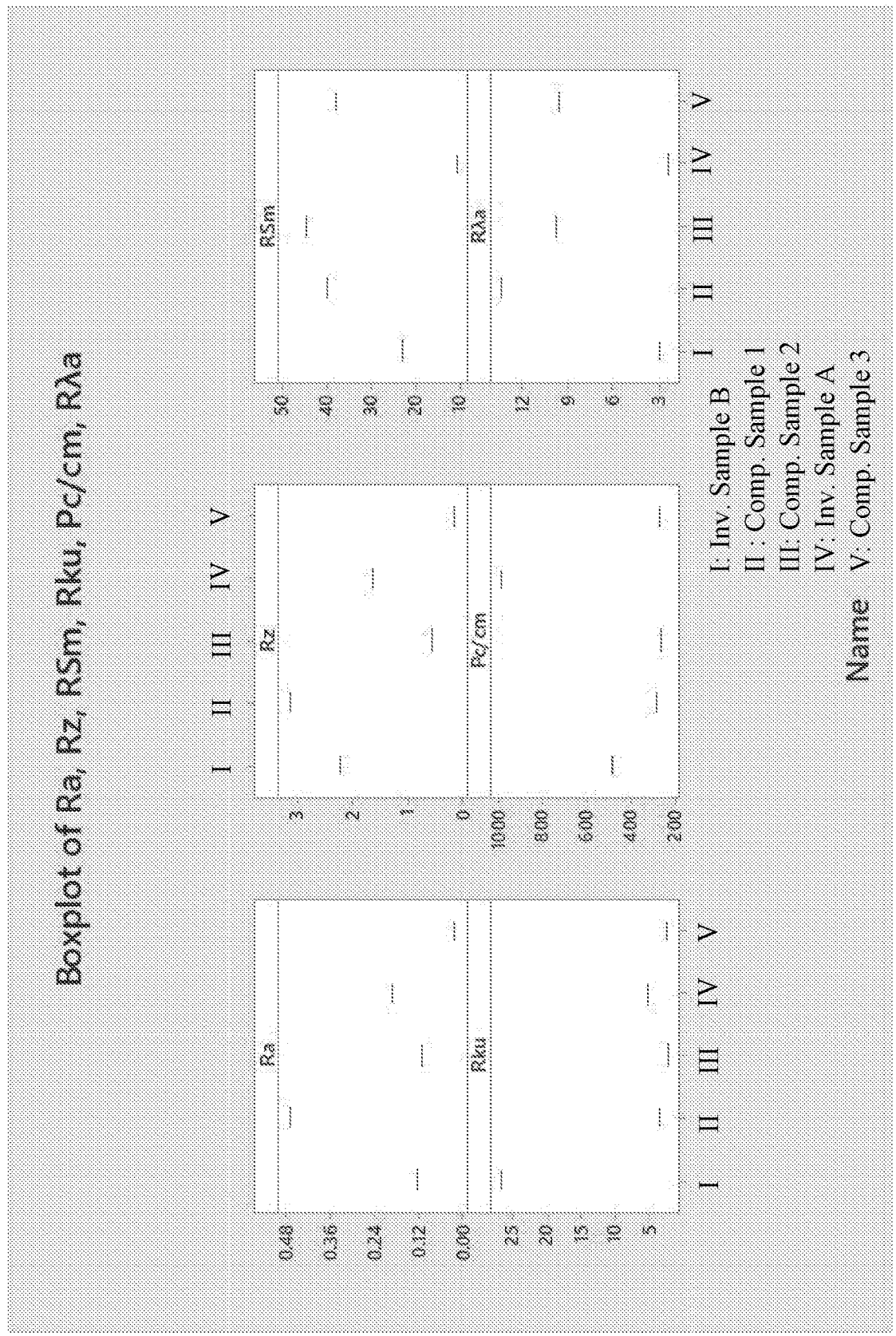
FIG. 10 is a graphical plot of various profile roughness parameters of samples of elastomeric articles manufactured by a method in accordance with an embodiment of the present invention and comparative articles.

Also, the profile roughness parameters of each sample were collected from a Mitutoyo Surftest profilometer using a low-force probe and are summarized in Table 2 and plotted in FIG. 10, where the y-axis is parallel to the longitudinal axis of the piston, such that the drug contact surface of the piston is positioned proximate the top of the graph. Optical images showing the surface topography of each sample taken from the 3D laser scanning confocal microscope are provided in FIGS. 19A, 20A, 21A, 22A and 23A, and surface topography of each sample is shown in FIGS. 19B, 20B, 21B, 22B and 23B.

TABLE 1

| Sample | Filter | Sa (μm) | Sz (μm) | Str | Spc (1/mm) | Sdr | Sku | Sal (μm) | Spd (1/mm²) |
|---|---|---|---|---|---|---|---|---|---|
| Inv. Sample A | None | 0.262336 | 4.1297 | 0.970222 | 9266.814 | 1.878123 | 5.158748 | 0.270005 | 1,259,318.00 |
| Inv. Sample B | None | 0.132787 | 12.2927 | 0.978388 | 5030.206 | 1.294387 | 59.67023 | 0.266522 | 1,015,401.00 |
| Comp. Sample 1 | None | 1.026478 | 15.1123 | 0.565495 | 4409.993 | 0.578164 | 5.76451 | 11.72558 | 420,438.90 |
| Comp. Sample 2 | None | 0.437393 | 4.5524 | 0.57411 | 792.3174 | 0.017666 | 5.438234 | 20.7215 | 500,808.00 |
| Comp. Sample 3 | None | 0.033312 | 1.2244 | 0.104636 | 261.1826 | 0.001726 | 58.54961 | 10.21932 | 978,239.60 |
| Inv. Sample A | 2 um | 0.082208 | 1.066229 | 0.634141 | 526.3015 | 0.022638 | 3.521474 | 8.831092 | 263,848.80 |
| Inv. Sample B | 2 um | 0.073382 | 3.471453 | 0.56019 | 357.6422 | 0.023383 | 21.87629 | 2.06764 | 206,612.20 |

TABLE 1-continued

| Sample | Filter | Sa (μm) | Sz (μm) | Str | Spc (1/mm) | Sdr | Sku | Sal (μm) | Spd (1/mm²) |
|---|---|---|---|---|---|---|---|---|---|
| Comp. Sample 1 | 2 um | 0.949232 | 12.7187 | 0.544209 | 656.7781 | 0.109784 | 5.733194 | 12.88502 | 55,100.75 |
| Comp. Sample 2 | 2 um | 0.435485 | 3.973141 | 0.444705 | 96.20823 | 0.005953 | 5.503678 | 18.76363 | 30,802.31 |
| Comp. Sample 3 | 2 um | 0.031641 | 1.039648 | 0.114469 | 19.44969 | 0.000249 | 70.06189 | 10.11807 | 100,523.70 |
| Inv. Sample A | 0.08 um | 0.176165 | 2.247206 | 0.746072 | 3599.218 | 0.50764 | 4.2981 | 0.561229 | 900,924.80 |
| Inv. Sample B | 0.08 um | 0.106901 | 7.796973 | 0.948766 | 1983.697 | 0.364732 | 41.39421 | 0.555849 | 704,039.70 |
| Comp. Sample 1 | 0.08 um | 1.007319 | 13.58936 | 0.562905 | 2201.081 | 0.322836 | 5.61202 | 12.19855 | 253,028.80 |
| Comp. Sample 2 | 0.08 um | 0.43421 | 4.395502 | 0.562864 | 400.5178 | 0.00996 | 5.406948 | 20.68207 | 248,452.10 |
| Comp. Sample 3 | 0.08 um | 0.033189 | 12.26598 | 0.134748 | 125.5913 | 0.002295 | 2699.859 | 9.075675 | 671,310.90 |

Results are at 50X objective.

TABLE 2

| Sample | Ra (μm) | Rz (μm) | RSm (μm) | Rku | Pc/cm | Rλa (μm) |
|---|---|---|---|---|---|---|
| Inv. Sample A | 0.195011 | 1.626049 | 10.28698 | 5.18205 | 986.5094 | 2.363367 |
| Inv. Sample B | 0.123327 | 2.244208 | 22.96563 | 26.7377 | 481.2344 | 2.973297 |
| Comp. Sample 1 | 0.473978 | 3.134142 | 39.95096 | 3.350478 | 282.9486 | 13.34772 |
| Comp. Sample 2 | 0.113927 | 0.568438 | 44.82615 | 2.058096 | 262.8811 | 9.818667 |
| Comp. Sample 3 | 0.025882 | 0.14815 | 37.9068 | 2.304411 | 272.3878 | 9.535636 |

Referring to Table 1, the parameters measured and/or calculated include arithmetic mean height (Sa), maximum height (Sz), texture aspect ratio (Str), arithmetic mean peak curvature (Spc), developed interfacial area ratio (Sdr), kurtosis (Sku), auto-correction length (Sal), and peak density (Spd). Arithmetic mean height is the average height of the absolute value with respect to the average height (non-absolute value) along the sampling length. Peak density is the number of peaks per unit area. For optical measurements, the smallest detectable peak is a function of the wavelength of the light source. Filtering the data is typically used to remove noise, but it may also be used to effectively define what qualifies as a peak.

As will be understood by one skilled in the art, although both arithmetic mean height and peak density are parameters used to characterize surface roughness, these parameters are not necessarily related to or correlated with each other. For example, when an elastomeric article covered by an inert film is molded (without a release layer), the inert film conforms to the surface of the mold, assumes the surface profile of the mold, and theoretically assumes the roughness of the mold. Thus, the peak density and the arithmetic mean height of the inert film are directly related to the peak density and arithmetic mean height of the mold. Subsequent surface treatments on the elastomeric article, such as burnishing, may reduce the height of some of the peaks and effectively reduce the arithmetic mean height. However, the peak density would not necessarily change as a result of these later surface treatments. Thus, arithmetic mean height and peak density cannot be considered to be parameters that can be correlated with each other.

Referring to Table 2, the parameters measured and/or calculated include arithmetic mean height (Ra), maximum height (Rz), mean width of profile elements (RSm), kurtosis (Rku), peaks per length (Pc/cm), and arithmetic wavelength (Rλa). The parameters shown in Table 2 represent measurements taken along a sampling line, whereas the parameters shown in Table 1 represent measurements taken over an area. The measurement results show that the inert film of Comp. Sample 2 likely assumed the surface profile and roughness of the mold during curing or vulcanization. The mean arithmetic heights (Sa) of the inert film of Inv. Samples A and B were noticeably better than that the mean arithmetic height (Sa) of the bare elastomer of Comp. Sample 1. Also, as can be seen in Table 1, the peak density (Spd) for Inv. Samples A and B increased compared to that of the inert film before molding (i.e., Comp. Sample 3). This is because the external surface of the release film conformed to the interior surface of the mold, while the inert film of Inv. Samples A and B assumed the surface profile and roughness of the release film. Thus, it is clear that the release film layer can be used to purposefully manipulate the surface texture of the inert film layer as a result of the release film layer and inert film layer mechanically interacting with each other during the molding process.

Moreover, during the molding process, the inert film layer 16 and the release film layer 46 are stretched around 400% as they are forced into the mold. Stretching the release film layer has two effects. First, surface features may proportionally decrease due to Poisson's ratio effectively reducing the mean arithmetic height, and second, features analogous to micro cracks may form, effectively creating new peaks and valleys. In addition, removing the release film layer 46 from the inert film layer 16 may create additional peaks. For example, localized contact areas of adhesion between the inert film layer 16 and the release film layer 46 may cause the surface of the inert film to stretch at the contact area when the release film layer 46 is peeled away until the adhesive bonds are broken. The stretching of the inert film 16 leaves residual deformation peaks on its surface.

That is, the inventors have surprisingly found that not only does the release film layer 46 protect the laminated film 23, 33 from damage, it actually improves the surface texture of the film. More particularly, the surface roughness, characterized by a peak density (with no filter applied), of the inert film 16 is increased by 3.8% to 28.7% by the molding process of the present invention in forming the laminated film 23, 33. The surface roughness, characterized by a peak density (when applying a Gaussian filter of 2.0 microns), of the inert film 16 is increased by from 105.5% to 162.5% by the molding process of the present invention in forming the laminated film 23, 33. The surface roughness, characterized by a peak density (when applying a Gaussian filter of 0.08 microns), of the inert film 16 is increased by from 4.9% to 34.2% by the molding process of the present invention in forming the laminated film 23, 33.

Also, in one embodiment, a sealing surface configured to contact the container or syringe along a mutual perimeter circumscribing the elastomeric article has a surface roughness characterized by a peak density greater than 50,000 peaks/mm$^2$ when applying a Gaussian filter of 2.0 microns or a peak density greater than 300,000 peaks/mm$^2$ when applying a Gaussian filter of 0.08 microns; preferably the sealing surface has a surface roughness characterized by a peak density greater than 100,000 peaks/mm$^2$ when applying a Gaussian filter of 2.0 microns or a peak density greater than 500,000 peaks/mm$^2$ when applying a Gaussian filter of 0.08 microns; more preferably the sealing surface has a surface roughness characterized by a peak density greater than 150,000 peaks/mm$^2$ when applying a Gaussian filter of 2.0 microns or a peak density greater than 600,000 peaks/mm$^2$ when applying a Gaussian filter of 0.08 microns; and most preferably the sealing surface has a surface roughness characterized by a peak density greater than 200,000 peaks/mm$^2$ when applying a Gaussian filter of 2.0 microns or a peak density greater than 700,000 peaks/mm$^2$ when applying a Gaussian filter of 0.08 microns.

With an extremely low, direction-independent surface roughness, elastomeric articles produced according to the present invention form an optimal interface with the container or syringe, and therefore yield improved CCI. The inventive elastomeric article is applicable for use in silicone-free systems, i.e., where there is no silicone oil to assist in mitigating CCI issues.

Figure 11:
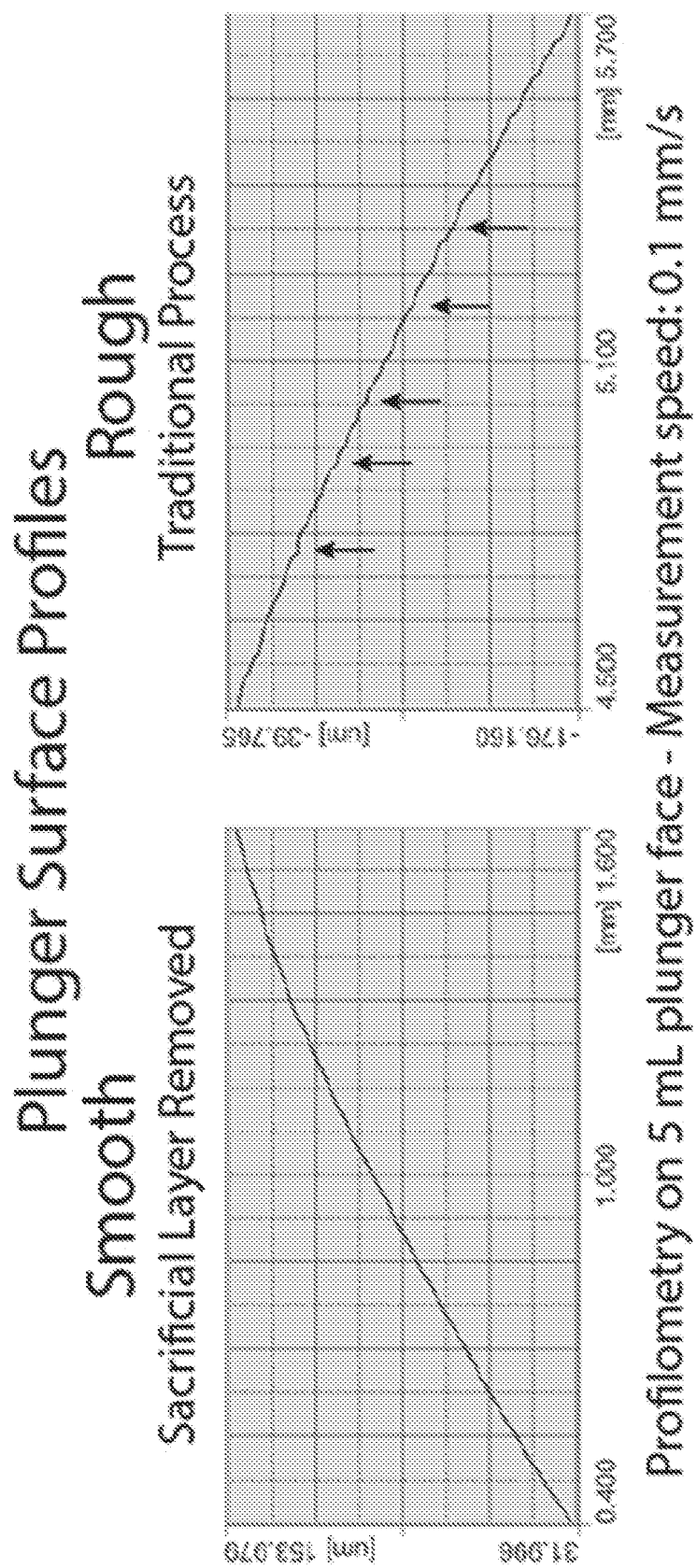
FIG. 11 graphically depicts single contact profilometry measurements to highlight the surface roughness difference between elastomeric articles produced according to the claimed invention and a conventional elastomeric article.
Figure 12:
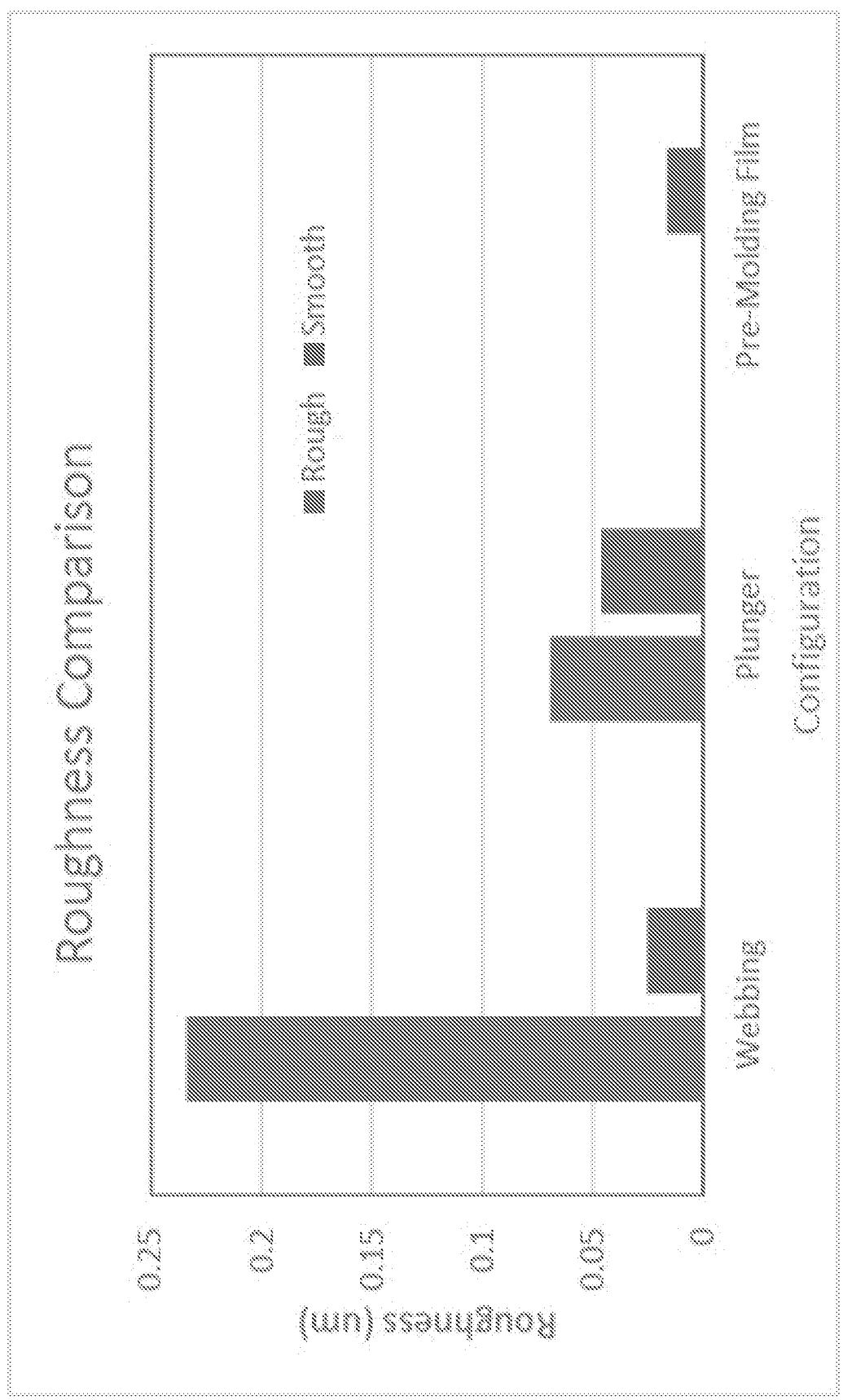
FIG. 12 graphically depicts the measurements of FIG. 11.

Also, graphically, there is a clear difference in the plots of the surface profile between the inventive elastomeric articles, produced using a release film layer, and conventional elastomeric articles, as shown in FIG. 11, even though the average numbers presented for piston faces in the graph (FIG. 12) do not appear drastically different. The curvature to the trace comes from the underlying curvature of the elastomer article. A collection of the quantitative measurements is summarized in FIG. 12.

The difference in surface finish discussed above is clearly visible in a qualitative visual evaluation. Images in FIG. 13 show an elastomeric piston according to the present invention, which has an improved surface finish appearing glossy (labeled as "Smooth"), as compared to those prepared by a conventional process not involving a release film layer appearing matte (labeled as "Rough"). The improved surface finish is evenly applied across the sidewall and crown surfaces, while the conventionally produced components possess a larger variability in texture across the visibly rough surface.

Test 2

In addition to Inv. Samples A and B and Comp. Samples 1-3, a number of 1-mL long elastomeric pistons provided with a laminated PTFE barrier film over the external sidewall and crown surfaces were produced according to the process described above with respect to FIG. 1, utilizing a release film layer formed of ETFE having a 2 mil (~50 μm) thickness (various tests were performed using pistons of this type, and are accordingly referred to in FIGS. 14, 15, 17, and 18 as Inventive Sample C) (Inv. Sample C); and a number of 1-mL long elastomeric pistons provided with a laminated ETFE barrier film over the external sidewall and crown surfaces were produced according to the same process parameters as used to produce Inv. Sample C (referred to in FIG. 16 as Inventive Sample D) (Inv. Sample D). For comparison purposes, a number of 1-mL long elastomeric pistons were produced using the same process parameters as that used to produce Inv. Sample C (i.e., having a laminated PTFE barrier film), but no release film layer was utilized (referred to in FIG. 14 as Comparative Sample 4) (Comp. Sample 4); and a number of 1-mL long elastomeric pistons were produced using the same process parameters as that used to produce Inv. Sample D (i.e., having a laminated ETFE film), but no release film layer was utilized (referred to in FIG. 16 as Comparative Sample 5) (Comp. Sample 5).

Figure 14:
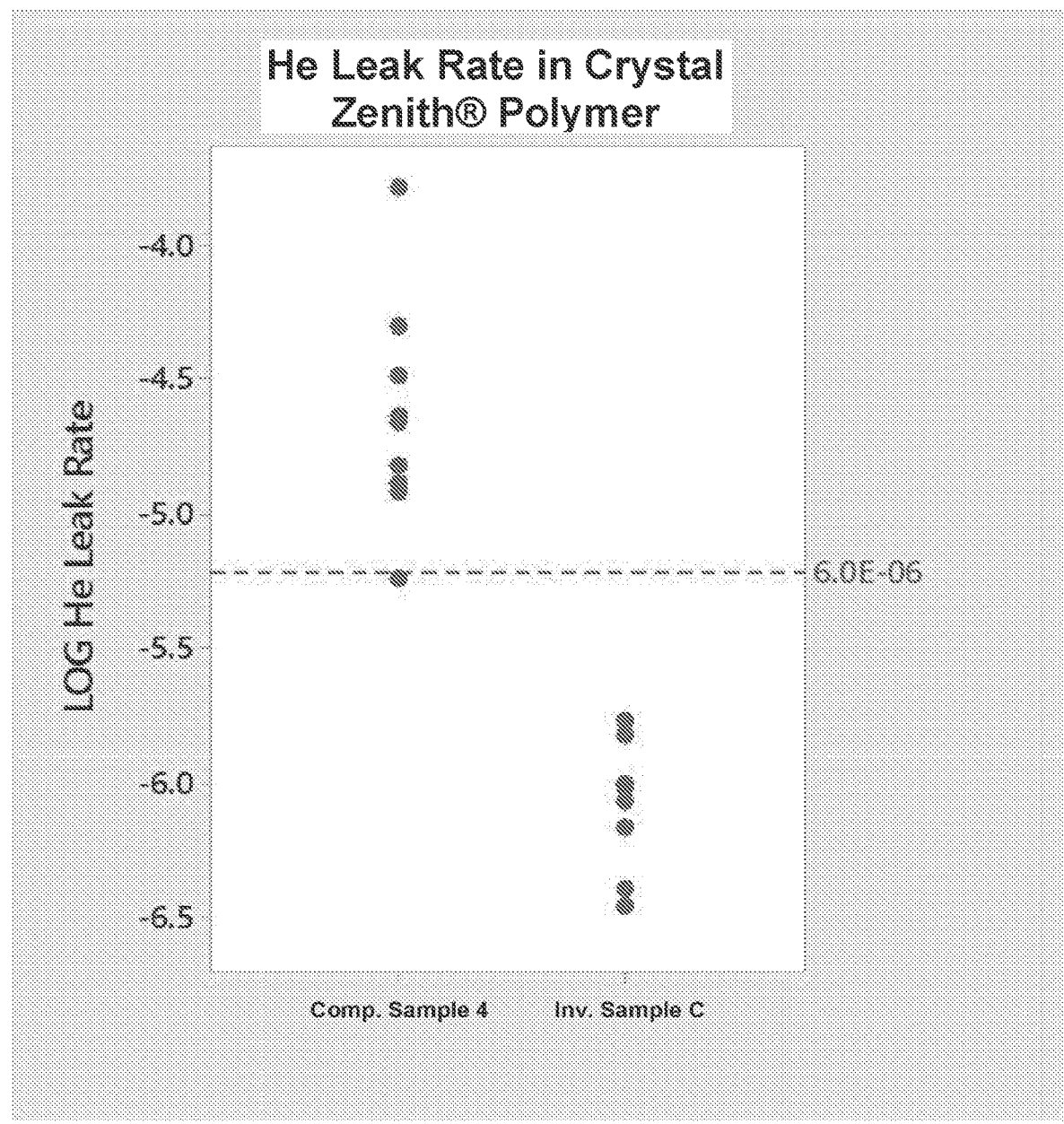
FIG. 14 illustrates CCI in a cyclic olefin polymer container, and more particularly a container formed of a polymer made and/or sold under the trademark Crystal Zenith® and sourced from Daikyo Seiko, Ltd. (hereinafter referred to as "Crystal Zenith® polymer), for Inventive Sample C and Comparative Sample 4 using helium leak testing.
Figure 15:
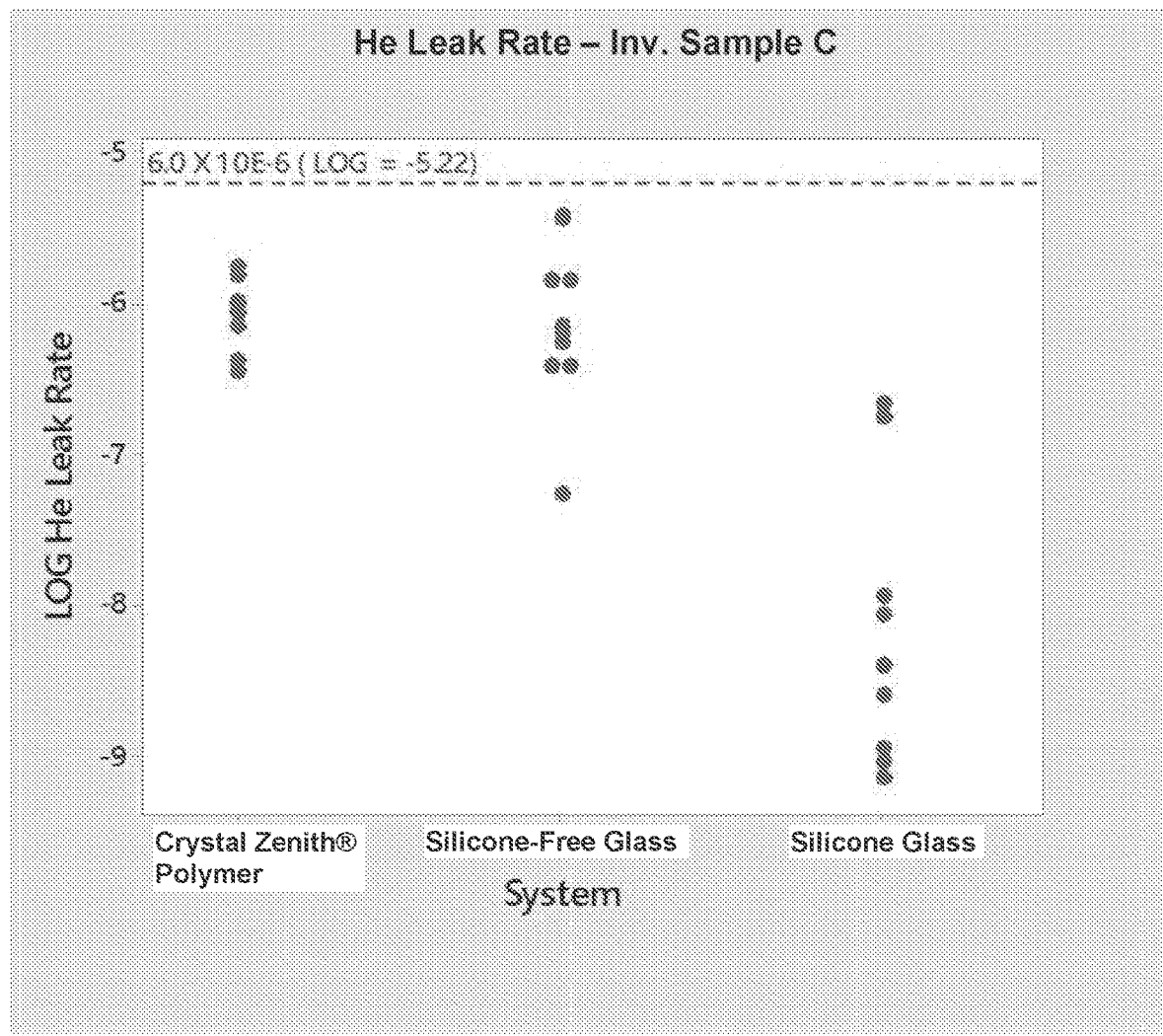
FIG. 15 illustrates CCI in Crystal Zenith® polymer, Silicone-Free Glass, and Baked-On Silicone Glass for Inventive Sample C using helium leak testing.
Figure 16:
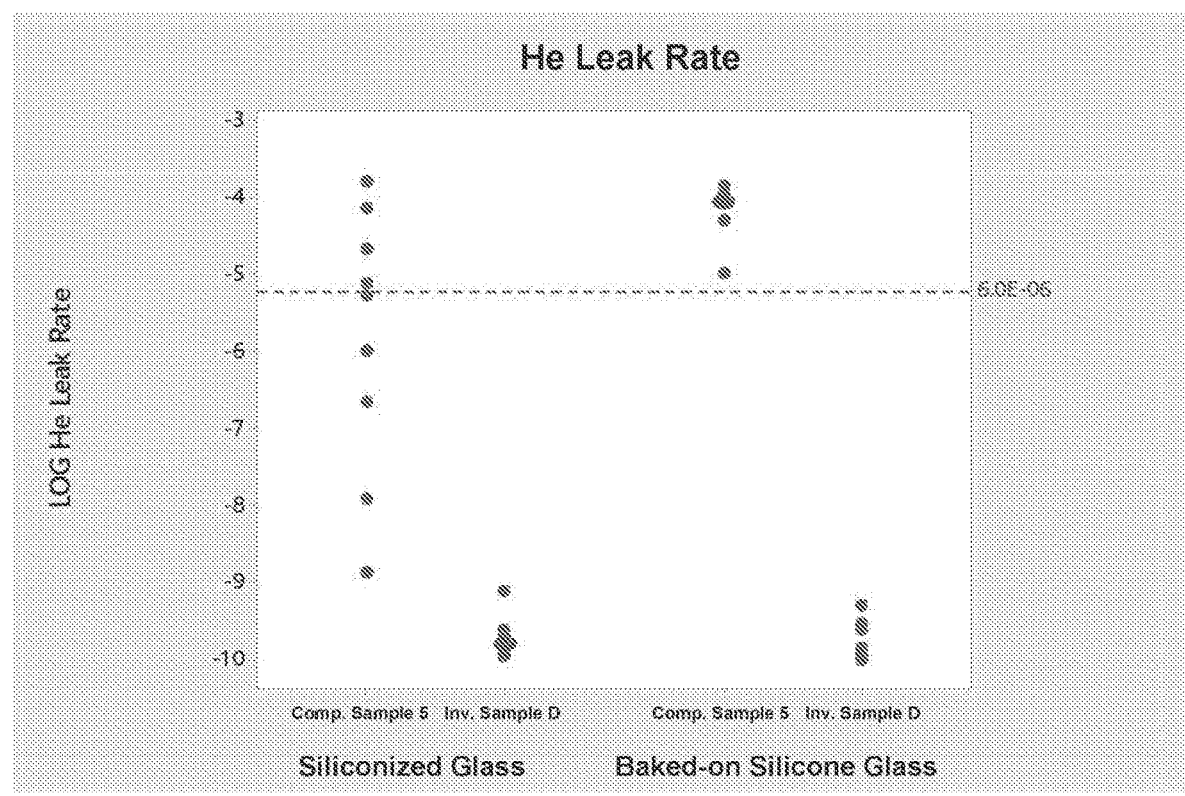
FIG. 16 illustrates CCI in Siliconized Glass and Baked-On Silicone Glass for Inventive Sample D and Comparative Sample 5 using helium leak testing.

FIG. 14 illustrates CCI in Crystal Zenith® polymer with PTFE laminated pistons produced with (Inv. Sample C) and without (Comp. Sample 4) release liners using helium leak testing. Similar to FIG. 14, FIG. 15 illustrates CCI in Crystal Zenith® polymer, Silicone-Free Glass, and Baked-On Silicone Glass with PTFE laminated pistons produced with release liners (Inv. Sample C) using helium leak testing. In addition, FIG. 16 illustrates CCI in Siliconized Glass, and Baked-On Silicone Glass with ETFE laminated pistons produced with (Inv. Sample D) and without (Comp. Sample 5) release liners using helium leak testing. The helium leak rate is an industry standard used to quantify the quality of a seal, using helium as an inert tracer gas. Though the same improved surface finish can be imparted to bare rubber articles through an omission of one film layer, CCI is not impacted by the change in surface roughness, likely because its viscoelastic flow fills surface defects under pressure. When the finished article is laminated by a polymer film, the film cannot flow and any surface imperfections (on either sealing surface) create a leakage path. FIGS. 14-16 illustrates the final roughness of the sealing surface is critical to performance and initial roughness of the film does not necessarily correlate to the functional performance under all circumstances. The threshold value of $6 \times 10^{-6}$ atm*cc/sec for sterility comes from the articles by Kirsch, et. al., titled "Pharmaceutical container/closure integrity," which is consistent with USP 1207. Although PTFE and ETFE were laminated pistons were produced for these experiments, one having ordinary skill would readily appreciate that other laminates would improve sealing performance of a rubber elastomer using a release liner.

Figure 17:
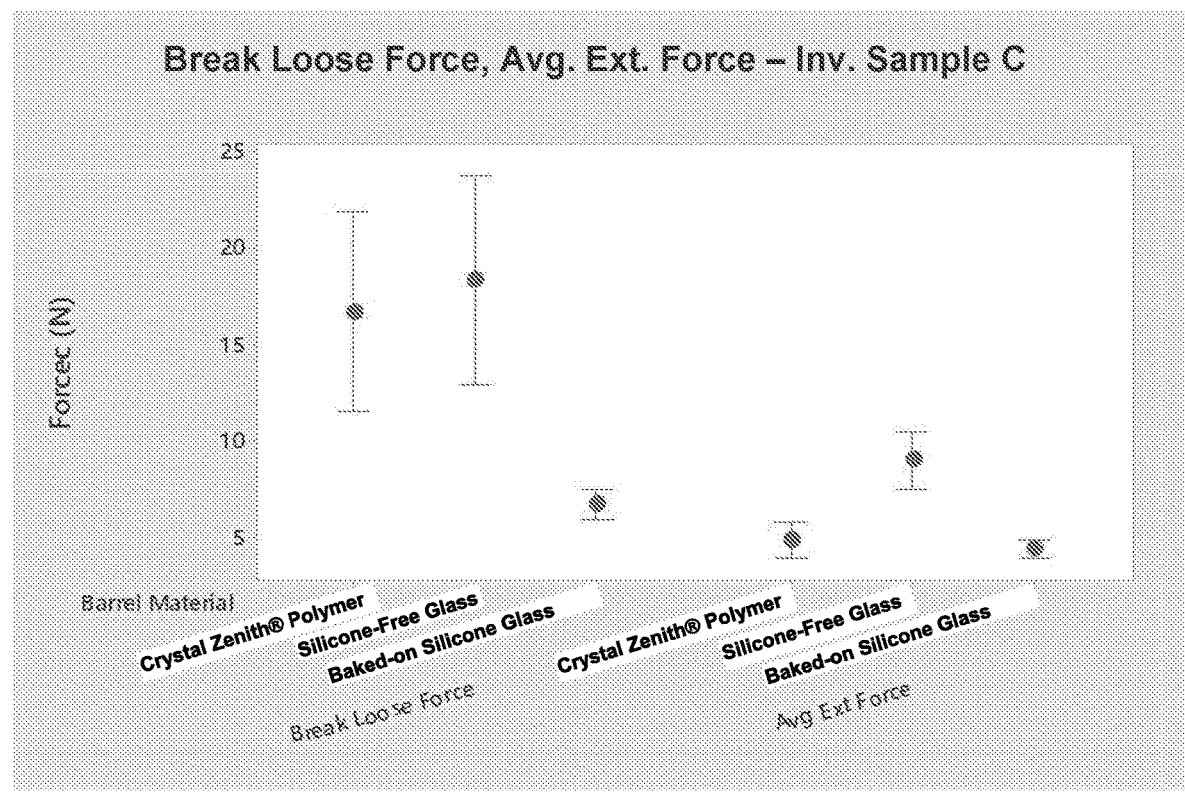
FIGS. 17 and 18 illustrate the force performance of Inventive Sample C.
Figure 18:
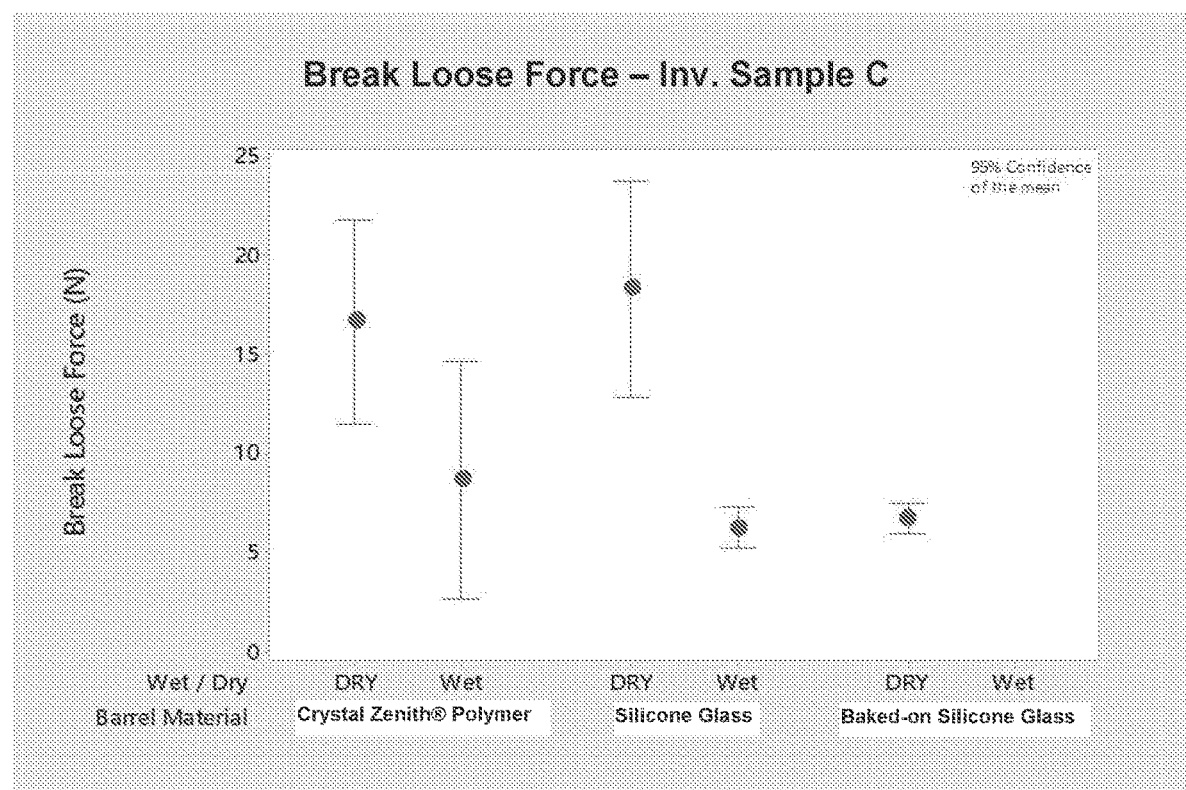
Figure 19A:
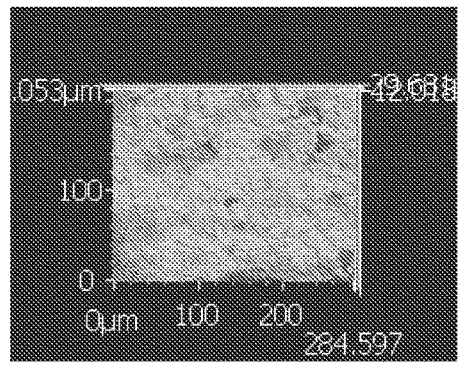
FIG. 19A depicts an enhanced optical image of the surface of Comparative Sample 1.
Figure 19B:
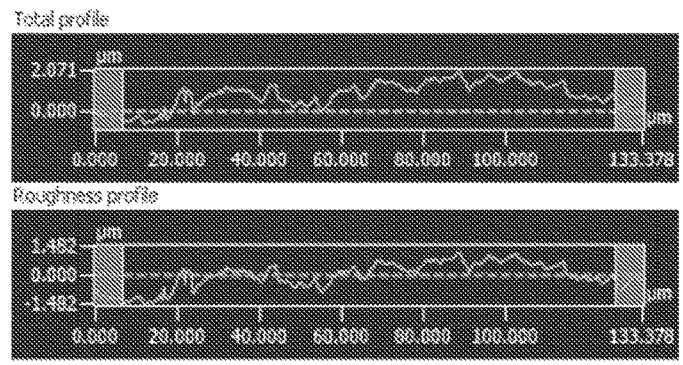
FIG. 19B depicts the waviness and roughness profiles of the surface of Comparative Sample 1.
Figure 20A:
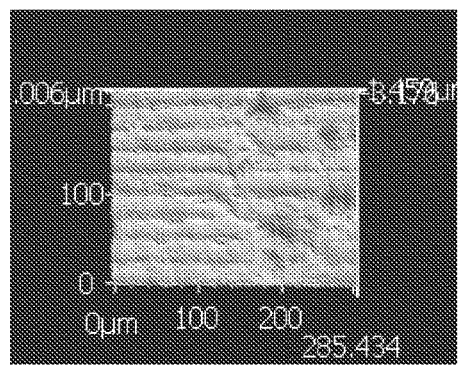
FIG. 20A depicts an enhanced optical image (intensity used to show depth and height) of the surface of Comparative Sample 2.
Figure 20B:
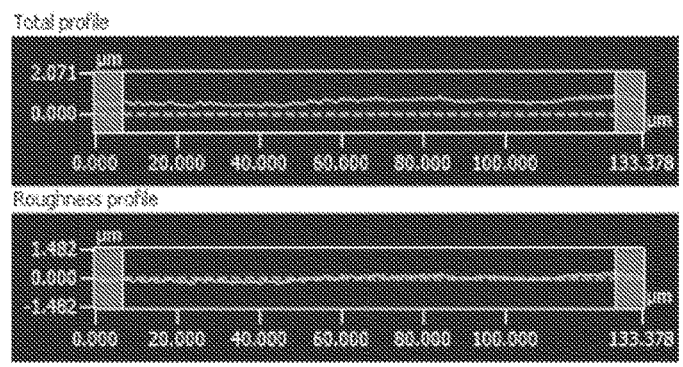
FIG. 20B depicts the waviness and roughness profiles of the surface of Comparative Sample 2.
Figure 21A:
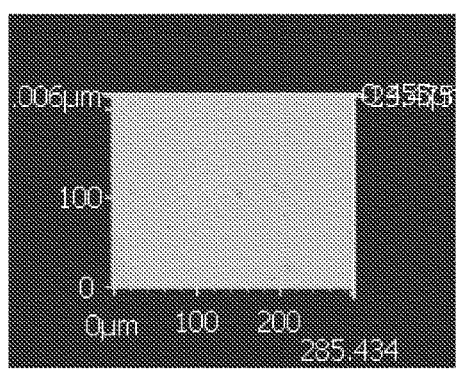
FIG. 21A depicts an enhanced optical image of the surface of Comparative Sample 3.
Figure 21B:
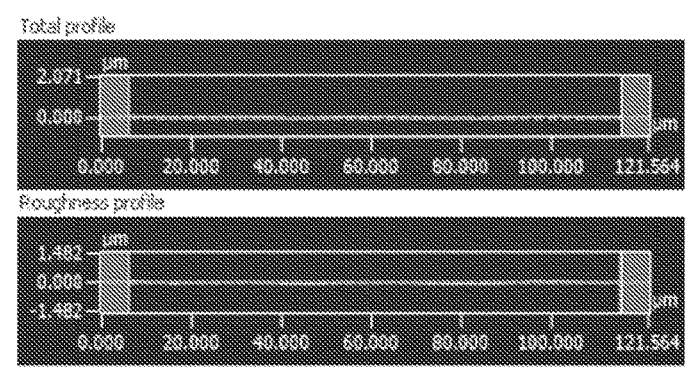
FIG. 21B depicts the waviness and roughness profiles of the surface of Comparative Sample 3.
Figure 22A:
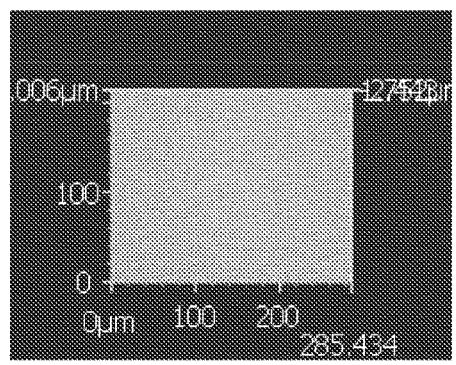
FIG. 22A depicts an enhanced optical image of the surface of Inventive Sample 1.
Figure 22B:
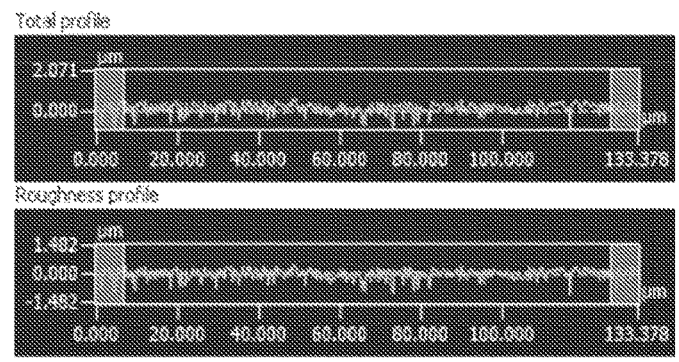
FIG. 22B depicts the waviness and roughness profiles of the surface of Inventive Sample 1.
Figure 23A:
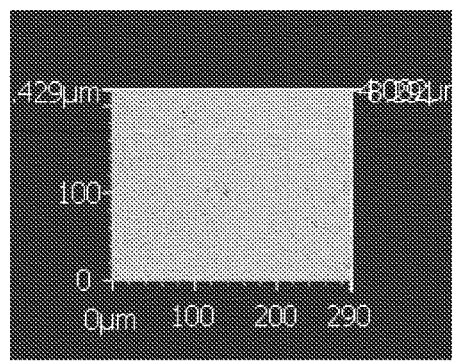
FIG. 23A depicts an enhanced optical image of the surface of Inventive Sample 2.
Figure 23B:
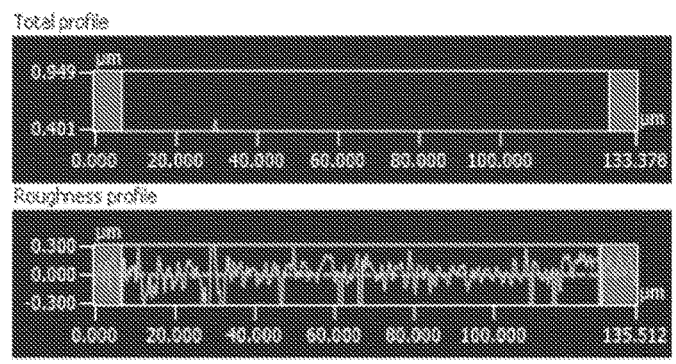
FIG. 23B depicts the waviness and roughness profiles of the surface of Inventive Sample 2.

FIGS. 17 and 18 illustrate the performance of PTFE laminated pistons produced with a release liner. Specifically, FIG. 17 illustrates the Break Loose Force and Average Extension Force for Inv. Sample C in Crystal Zenith® polymer, Silicone-Free Glass, and Baked-On Silicone Glass under dry conditions using an Instron BLE method at 304.8 mm/min. FIG. 18 illustrates the Break Loose Force for Sample C in Crystal Zenith® polymer, Silicone-Free Glass, and Baked-On Silicone Glass under dry and wet conditions using an Instron BLE method at 304.8 mm/min (note tests were not conducted for Sample C in Baked-On Silicone Glass under wet conditions). As with the marked improvement in the sealing performance, PTFE laminated pistons produced with a release liner have similar Break Loose Force and Average Extension Force characteristics as some commercially available pistons that require the use of silicone oil (although commercially available pistons used with silicone oil were not tested in this experiment). The improved force performance is due to the entire contacting surfaces of the piston (i.e., the sidewall and crown surfaces) being coated with a lubricious inert film rather than only the drug interface surface as is typically done (if at all) for pistons intended to be used with silicone oil. Although this experiment only characterized the force performance of PTFE laminated pistons, one having ordinary skill in the art would appreciate that ETFE and other laminated pistons produced with a release liner would also have improved force characteristics in various barrel configurations.

The present method could also be used to make an elastomeric article without any laminated film layer (i.e., bare elastomer protected during molding process by release film layer 46). Other surface modifications may include chemical functionalization, coatings requiring a smooth substrate.

A superior control of surface roughness may enable tunability of total contact area, and therefore improve other functional attributes (i.e., break loose and extrusion forces). Similarly, this may enable product geometries not previously possible.

This product could similarly be prepared through the design of new molds. Other possible production methods include, but are not limited to, polished molds, molds without sharp features (to avoid film damage), PTFE (or other polymer) coated molds, alternate mold materials (i.e. polymer or ceramic), alternate mold-release technologies. However, due to the how the release film layer protects the inert film layer from surface features of the mold, the invention lends itself well to rough molds and may extend the service life of any mold—ultimately reducing costs.

The invention could be advantageously used in any type of seal used to contain or contact injectable drugs. This includes, but is not limited to pistons, stoppers, and lined seals. The greatest need for the invention is in silicone-free containment systems for injectable medicines, because CCI is critical to maintain in these systems. The invention is more advantageously used for sensitive biologic drugs and intraocularly deliverable drugs. The invention could also be advantageously used to reduce manufacturing costs for any elastomer for containment of injectable medicine which has good barrier properties.

The inventive technology could be used for production of fully or partially-film laminated pistons, stoppers, etc., and/or silicone-free closure systems with barrier properties. Preferably, the inventive technology is used for production of fully-film laminated pistons, stoppers, etc., and/or silicone-free closure systems with barrier properties.

Certain terminology is used in the following description for convenience only and is not limiting. The words "proximal," "distal," "upward," "downward," "bottom," and "top" designate directions in the drawings to which reference is made. The words "inwardly" and "outwardly" refer to directions toward and away from, respectively, a geometric center of the device, and designated parts thereof, in accordance with the present invention. Unless specifically set forth herein, the terms "a," "an," and "the" are not limited to one element, but instead should be read as meaning "at least one." The terminology includes the words noted above, derivatives thereof and words of similar import.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

We claim:

1. A method for manufacturing an elastomeric stopper or piston, the method comprising:

placing, into a mold, an assembly of an uncured elastomeric sheet, an inert film fully covering the elastomeric sheet, and a release film covering the inert film, such that the release film is in contact with and positioned between the inert film and an interior surface of an open cavity of the mold, the inert film having an initial surface roughness characterized by an initial peak density;

compression molding the assembly in the mold, such that the assembly is forced into the open cavity, the elastomeric sheet is cured, and the inert film is laminated onto the elastomeric sheet to form a laminated article, whereby localized contact areas between the inert film and the release film are stretched during said forcing so as to increase surface roughness of the inert film to a second surface roughness characterized by a second peak density that is greater than the initial peak density; and removing the release film from the laminated inert film.

2. The method of claim 1, wherein the second peak density is increased by at least 3% relative to the initial peak density.

3. The method of claim 1, wherein the second peak density is increased by at least 25% relative to the initial peak density.

4. The method of claim 1, wherein the second peak density is increased by 3% to 165% relative to the initial peak density.

5. The method of claim 1, wherein the second peak density is increased by 25% to 35% relative to the initial peak density.

6. The method of claim 1, wherein the second peak density is greater than 50,000 peaks/mm$^2$ when applying a Gaussian filter of 2.0 microns or greater than 300,000 peaks/mm$^2$ when applying a Gaussian filter of 0.08 microns.

7. The method of claim 1, wherein the second peak density is greater than 100,000 peaks/mm$^2$ when applying a Gaussian filter of 2.0 microns or greater than 500,000 peaks/mm$^2$ when applying a Gaussian filter of 0.08 microns.

8. The method of claim 1, wherein the second peak density is greater than 150,000 peaks/mm$^2$ when applying a Gaussian filter of 2.0 microns or greater than 600,000 peaks/mm$^2$ when applying a Gaussian filter of 0.08 microns.

9. The method of claim 1, wherein the second peak density is greater than 200,000 peaks/mm$^2$ when applying a Gaussian filter of 2.0 microns or greater than 700,000 peaks/mm$^2$ when applying a Gaussian filter of 0.08 microns.

10. The method of claim 1, wherein the laminated article is the piston.

11. The method of claim 1, wherein the laminated article is the stopper.

12. The method of claim 1,
wherein an external surface of the laminated inert film is substantially free of striations.

13. The method of claim 12, wherein the external surface of the laminated inert film has a mirror-like finish.

14. The method of claim 1, wherein the inert film is comprised of a fluoropolymer.

15. The method of claim 1, wherein the laminated article is configured to be utilized as a silicone-free elastomeric stopper or piston.

16. The method of claim 1, wherein the mold comprises an upper mold half defining a plurality of protrusions and a lower mold half, and wherein the open cavity is one of a plurality of open cavities defined in the lower mold half with each of the open cavities corresponding to a respective one of the protrusions of the upper mold half.

17. The method of claim 1, wherein compression molding the assembly in the mold comprises vulcanizing the elastomeric sheet under heat and pressure so as to become non-detachably joined to the inert film.

18. The method of claim 1, wherein compression molding the assembly in the mold is carried out at a temperature of 120° C. to 310° C. under a pressure of about 40 to 350 kg/cm$^2$ and for a duration of from a few seconds to 30 minutes.

\* \* \* \* \*